United States Patent [19]
Elliott

[11] Patent Number: 5,443,753
[45] Date of Patent: * Aug. 22, 1995

[54] REACTION PRODUCTS OF LYOTROPIC LIQUID CRYSTAL SALT COMPLEXES

[76] Inventor: Stanley B. Elliott, 7125 Conelly Blvd., Walton Hills, Ohio 44146

[*] Notice: The portion of the term of this patent subsequent to Jan. 21, 2009 has been disclaimed.

[21] Appl. No.: 239,619

[22] Filed: May 9, 1994

Related U.S. Application Data

[60] Continuation of Ser. No. 954,556, Sep. 30, 1992, Pat. No. 5,354,499, which is a continuation-in-part of Ser. No. 821,084, Jan. 16, 1992, Pat. No. 5,354,496, which is a continuation-in-part of Ser. No. 642,009, Jan. 16, 1991, abandoned, which is a continuation-in-part of Ser. No. 562,017, Aug. 2, 1990, Pat. No. 5,082,588, which is a division of Ser. No. 444,559, Dec. 1, 1989, Pat. No. 4,975,249, which is a continuation of Ser. No. 78,186, Jul. 27, 1987, abandoned.

[51] Int. Cl.$^6$ .............................................. C09K 19/52
[52] U.S. Cl. .............................. 252/299.01; 252/299.6; 428/1
[58] Field of Search ............... 252/299.01, 299.62, 252/299.6; 428/1

[56] References Cited

U.S. PATENT DOCUMENTS

| | | | |
|---|---|---|---|
| 5,082,588 | 1/1992 | Elliott | 252/299.62 |
| 5,354,496 | 10/1994 | Elliott | 252/299.01 |
| 5,354,499 | 10/1994 | Elliott | 252/299.01 |

Primary Examiner—Shean Wu
Attorney, Agent, or Firm—Marshall & Melhorn

[57] ABSTRACT

The invention provides novel polymeric and non-polymeric, liquid crystal type, chemical salt complexes of aroyl acids and monovalent and polyvalent metals. They are formed by covalent and coordinate bonding for use as electrical superconductors, as electrolytes in alkali metal batteries, electrochromic windows, static dissipative polymers, etc. The invention also provides processes for manufacturing such complexes, including the in situ formation in and on various metals and oxides. The processes also include the use of supercritical solvents such as carbon dioxide to solubilize the complexes for introduction into plastics and inorganic superconductors. The chemical complexes include the triads formed of liquid crystal aroyl salts, non-polymeric ligand solvents, and polymeric aroylacrylate salts. Both homopolymer and copolymer complexes of the metal aroylacrylates may be prepared and the latter may be cross-linked. Novel covalent, liquid crystal, reaction product complexes of lyotropic liquid crystal, metal aroylacrylate complexes and isocyanates (both polymeric and non-polymeric) are prepared. These are dyes having a high degree of conjugated unsaturation. Solutions of the reaction products of monovalent and polyvalent metal complexes can be prepared. Excess ligand solvents used in preparing these materials can be vaporized in a controlled way to produce liquid crystal systems. These systems can be cross-linked. Supercritical fluids such as carbon dioxide can be used to dissolve these various complexes and allow their distribution into both plastic particles and powdered inorganic superconductors so as to distribute complexes uniformly throughout the particles so as to enhance properties such as electrical conductivity when the particles are formed into larger systems.

10 Claims, 4 Drawing Sheets

REACTION PRODUCTS OF LYOTROPIC LIQUID CRYSTAL SALT COMPLEXES

This is a continuation of application Ser. No. 07/954,556, filed on Sep. 30, 1992 now U.S. Pat. No. 5,354,499 which is a continuation-in-part of my application Ser. No. 07/821,084 filed Jan. 16, 1992, now U.S. Pat. No. 5,354,496 issued Oct. 11, 1994, which is a continuation-in-part of my application Ser. No. 07/642,009 filed Jan. 16, 1991, now abandoned, which is a continuation-in-part of my application Ser. No. 07/562,017 filed Aug. 2, 1990, now U.S. Pat. No. 5,082,588, which is a division of patent application Ser. No. 07/444,559 filed Dec. 1, 1989, now U.S. Pat. No. 4,975,249, which is a continuation of Ser. No. 07/078,186 filed Jul. 27, 1987 now abandoned.

BACKGROUND OF THE INVENTION

In my pending patent application, U.S. Ser. No. 763,003, I have noted that scores of hygrometric devices have been developed in response to a world wide need among modern societies for the indication and control of the humidity of myriad processes and locations in commerce, industry, and the sciences. I particularly stressed that nearly all of these devices have been "secondary" types which depend on non-reproducible processes such as moisture sorption by various materials. As a result, the devices have no inherent accuracy, they drift badly over a period of time, and they are not suitable for myriad demanding needs.

In my pending application I noted that only a few inherently accurate "primary" type devices based on unvarying physical phenomena have been developed. These have been characterized by high cost, high power consumption, and large sensor bulk and equipment size. Heading the short list of primary devices has been the "dew temperature" or "cold mirror" hygrometer.

My pending application describes a new type of primary optical hygrometer in which the mirror is heated instead of chilled. It is analogous to the cold mirror hygrometer but it is highly superior because of its smaller size and lower power consumption. However, in spite of its general excellence for many applications, neither it nor the cold mirror hygrometer is suited for the overall ultra-miniaturization found in ICs (integrated circuits) or VLSICs (very large scale integrated circuits). This is because substantial but variable cooling or heating of the integrated circuits which are intimately associated with the operation of the sensor mirror introduces complex non-linearity problems and radiation effects.

In response to the urgent need for miniature military radiosondes, humidity sensors to incorporate within VLSIC "packages," and other critical applications, humidity sensors have been developed by others. These depend on the change of electrical capacitance of various dielectric materials as the humidity over the materials varies. However, these sensors are of the secondary type in which the moisture (which causes the dielectric constant change in the dielectric material) is sorbed in a non-linear and non-reproducible way which shifts with time. Thus, if the sensor is accessible (as in a radiosonde) a very difficult field standardization of the sensor must be attempted before sending the balloon aloft. If the sensor is sealed into a VLSIC package to monitor its interior, there is no way to check and compensate for the sensor's drift. Thus, what has been sorely needed is a capacitance-type, primary standard humidity device which a) operates at ambient temperature, b) has a sensor which is invariant, and c) has a mode for quickly checking for electronic circuit problems.

The sensors of the present invention are unusual in that the humidity-responsive sensors generate concurrent primary optical-type and primary capacitance-type signals. Even well designed and properly manufactured integrated circuits can abruptly develop circuit problems. These can result in false humidity readouts even though the capacitance/humidity changes of these sensors are invariant. With these new sensors an ongoing monitoring of the soundness of the electronics of devices which utilize the sensors in the capacitance mode can be readily provided by simultaneously optically monitoring the sensor. For example, providing a small window in one of the capacitance electrodes will allow the sensor film to be seen. It will show a dark field/bright field shift every time the gases over the sensor reach a known, precise, invariant humidity. A readout of this humidity should appear concurrently, of course, on the display screen of the capacitance meter. If desired, for convenience the same sensor material as is used between the capacitance electrodes can be optically displayed elsewhere in the system which transports the gas across the capacitance electrodes/sensor film for measurement.

The use of spatially separated dual sensors of the same composition, one sensing optically and the other capacitively, has the additional merit of allowing one to readily optimize the thickness of each for its particular function. Thus, an optical-type, humidity-responsive sensor might be coated at a thickness of about 0.01 min. in order to secure a brilliant readout. However, a capacitance-type sensor might be coated more thinly since the capacitance and the sensitivity of an "electrode/humidity-responsive dielectric composition/electrode" triad increases, as the thickness of the dielectric composition decreases. If dual sensors are not convenient, a very small area of a very thinly coated sensor film being monitored capacitively may be of greater thickness so that when scanned optically a brilliant optical readout results.

In my U.S. Pat. Nos. 3,776,038, 4,166,891 and 4,175,207 I describe optical type, humidity-responsive devices of great utility which cover the middle range of relative humidity. However, in computer science, electronics in general and other specialized fields, the extreme humidity ranges are of special importance because of the corrosive effect of water condensing in equipment at very high humidities and static sparks (electrostatic discharges) damaging microelectronics at very low humidities. Both in electronic capacitive-responsive devices and in direct optical readout devices the sensors of the new technology allow covering the relative humidity (RH) range down to 15% and below and 85% and above. Thus, their primary, invariant qualities allow precise monitoring of ranges which until now have been notorious for generating badly drilling signals since the sorption processes used by ordinary hygrometers become increasingly erratic at very high and very low humidities.

SUMMARY OF THE INVENTION

The present invention provides novel chemical compositions for use in primary standard, optical/capacitance-type or optical-type or capacitance-type hygrometric devices. It also provides methods for using these compositions as sensors for the precise measurement of the humidity of gases as well as the apparatus.

As a result of extensive research I have discovered novel chemical compounds which function in a new and unexpected way to indicate the ambient humidity through changes in optical properties and/or electrical capacitance. I have also discovered what I term "lattice modifiers", novel compounds to extend the humidity ranges covered by the basic sensors. Further, I have devised compounding methods for the sensors and sensors/lattice modifiers which make them suitable for production coating and utilization in a variety of hygrometers, controls, and humidity-sensing devices.

The devices and methods of the new hygrometry allow many variations on the primary requirements. For example, if the sensors are to be operated in the optical mode, light sources such as LEDs, tungsten lamps, neon lamps, etc. can be used with a variety of light detecting means such as photo-transistors, photo-SCRs, photo-diodes, photo-resistor cells, the human eye, etc. If amplification of the optical change is desired, circular-type polarizers can be used with reflection systems and crossed-linear-type polarizers can be used with transmission systems. If the sensors are to be operated in the electrical capacitance mode, electrical power of various voltages can be used. Frequencies used may range from direct current to radio frequencies, though I have found a 3–10 volt signal at 1000 Hz a convenient source. Various capacitance measuring devices of good accuracy are readily available, the meters widely used for measuring the capacitance of capacitors proving quite suitable. If desired, the sensor can be made an integral part of a capacitance-sensitive IC. Thus, a humidity-induced change in the dielectric constant of the sensor of the IC device produces a proportional change in the output of the IC device.

The sensors used for capacitance mode sensing can be of widely varying area and thickness depending on the electronics used for indicating and/or recording and the applications of the device. Electrode spacing can be varied, and electrode materials of various types can be used so long as they are not corroded by the humid gases being sampled or by the sensor compounds.

A number of modes of placing electrodes have been used by workers in this field and most of these work nicely. These include co-planar interdigitated electrodes, parallel plate electrodes, and co-planar series connected electrodes. Opposed, planar electrodes, with the upper electrode perforated so that the monitored gas reaches the sensor film which is coated onto the lower electrode work well. To prevent electrical conduction through the sensor compound, the upper or lower electrode can be coated with a very thin film of insulating polymer, or an air space can be left between the sensor film and the upper, perforated electrode.

The use of co-planar, polymer insulated, interdigitated electrodes coated with the humidity sensing material also can be used. Often, a gas permeable, light weight secondary electrode is floated on the surface of the sensor film over the interdigitated electrodes so as to secure a higher electrode area exposure than can be secured from only the edges of interdigitated electrodes. If desired, two or more sensor films covering contiguous humidity ranges can be applied to the electrode in a coplanar, contiguous manner so as to cover an exceptionally broad humidity range. Or, an electrode bearing a sensor film covering one humidity range can be covered with a humidity permeable, diffusion-blocking polymer film and then coated with a sensor film covering a contiguous humidity range. The second electrode is then located appropriately above the multiple-sensor layer film.

The FIG. references which follow refer to the chemical and physical responses to water of the lyotropic liquid crystal salts of my parent patent. They also describe various embodiments of humidity responsive devices based on the use of such chemical compositions. They are not pertinent to the present continuation-in-part application. The parent application is Ser. No. 07/078,186 filed Jul. 27, 1987, entitled "Optical and Capacitance Type, Phase Transition Humidity,Responsive Devices."

THE DRAWINGS

Figure 8A:
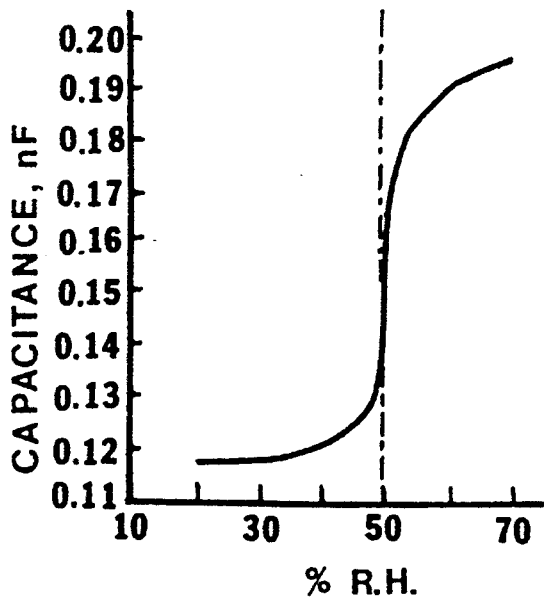

FIG. 8a is a capacitance vs. RH curve for an alkali metal complex humidity sensor much as claimed in U.S. Pat. No. 4, 166,891.

Figure 8B:
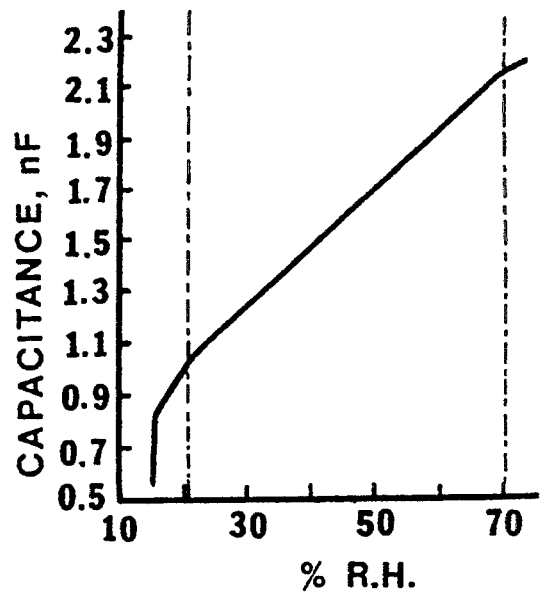

FIG. 8b is a capacitance vs. RH curve for the humidity sensor cesium benzoylpropionate.

Figure 8C:
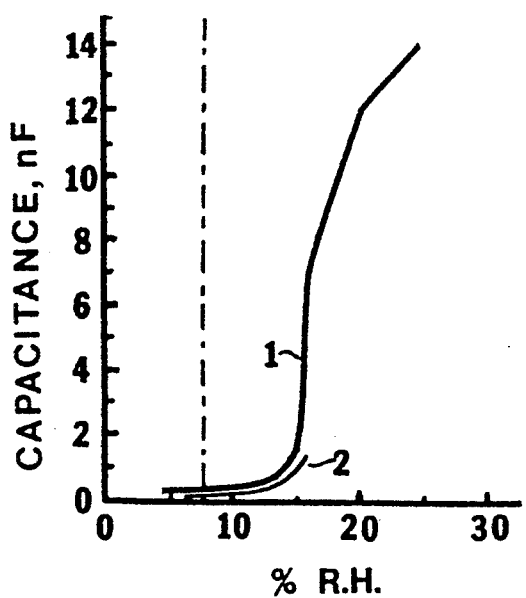
Figure 8D:
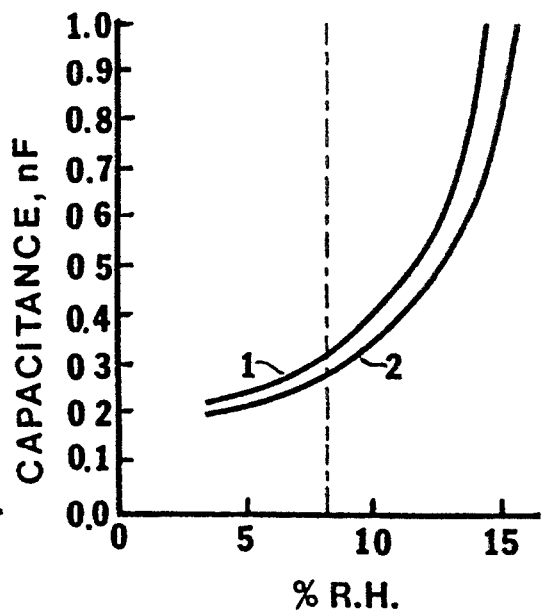

FIG. 8c are capacitance vs. RH curves before and after thermal processing for a humidity sensor comprising calcium chloride compounds with silica; and FIG. 8d is an enlarged section of the capacitance vs. RH curves of FIG. 8c.

DETAILED DESCRIPTION OF THE INVENTION

In my U.S. Pat. Nos. 3,776,038, 4,166,891, and 4,175,207 I claim sensor compositions which undergo two phase shifts, namely, from an isotropic solid to an anisotropic solid and then, at higher humidities, from an anisotropic solid to an isotropic solution (usually used in a gelled state). This can be summarized thus:

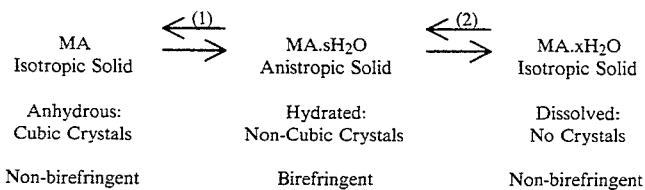

Though this dual signalling has worked well for direct readout devices, electronic devices can be more simply designed if the sensor undergoes only an unambiguous "on/off" or "birefringent/non-birefringent" shift. The novel sensors of the present invention undergo only phase shift (2) shown above. This is a reversible shift between an anisotropic (birefringent) crystal and an isotropic solution (non-birefringent).

Figure 1:
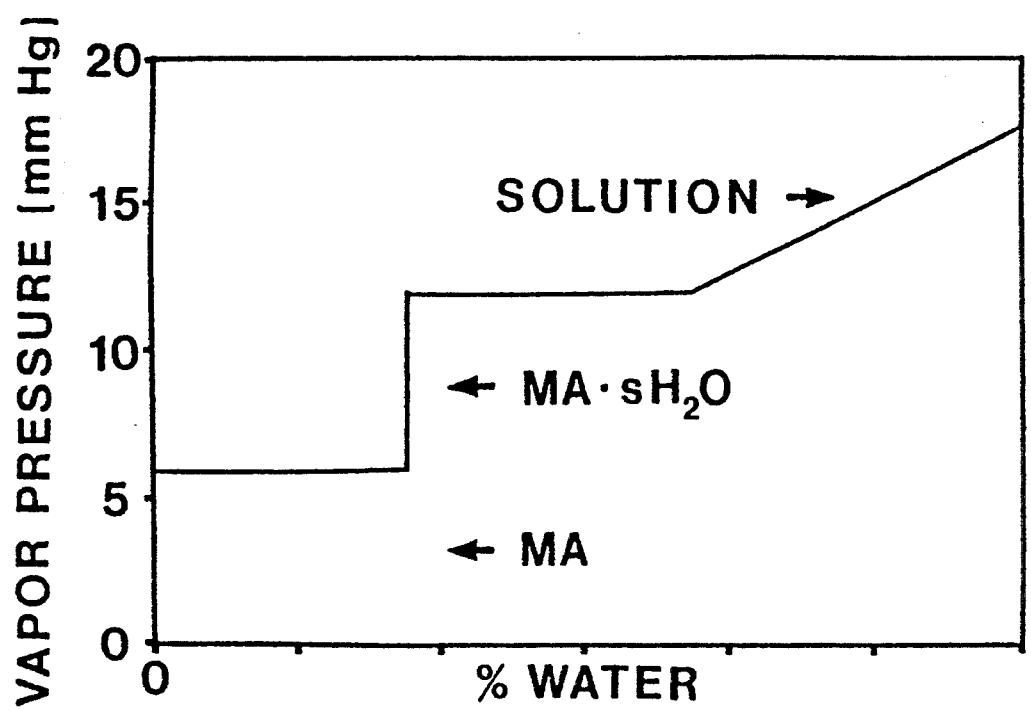
FIG. 1 is a vapor pressure curve for hydrates of a typical salt, MA (Where M is a metal cation and A is an acid radical), at 20° C.

These mechanisms can be described simply with reference to FIG. 1. If we increase the vapor pressure of water in the presence of the sensor salt MA no reaction occurs until a critical vapor pressure is reached. Then a hydrate, MA.sH$_2$O, with s representing a specific molecular ratio, starts to form. Any attempt to increase the water vapor pressure is then countered by the formation of more hydrate until all of the MA has reacted. Only then can the water vapor pressure increase. Because of the relatively easy removal or addition of water, the hydrate water is specifically indicated as H$_2$O, though it is chemically bound.

If the water vapor pressure increases still more, the hydrate deliquesces. That is, the compound removes water from the surrounding atmosphere to form an isotropic solution. All soluble salts are deliquescent when the partial pressure of the water vapor in the atmosphere exceeds the water vapor pressure of their saturated solution. Though the birefringent, anisotropic sensor salt in the phase equilibria shown above (and illustrated in FIG. 1 ) is hydrated (MA.sH$_2$O), birefringent salts can also be anhydrous. In such a case, the anhydrous birefringent salt directly deliquesces to a non-birefringent, isotropic solution. Once all of the salt has dissolved, a further increase of water vapor pressure brings dilution of the saturated solution. This technology uses the crystal/solution phase shift point for optical signalling because it occurs at a very precise and reproducible humidity and temperature. The salts may be gelled so that the sensor passes from opalescent, anisotropic films to clear, isotropic gels at the optical signalling point.

Figure 2:
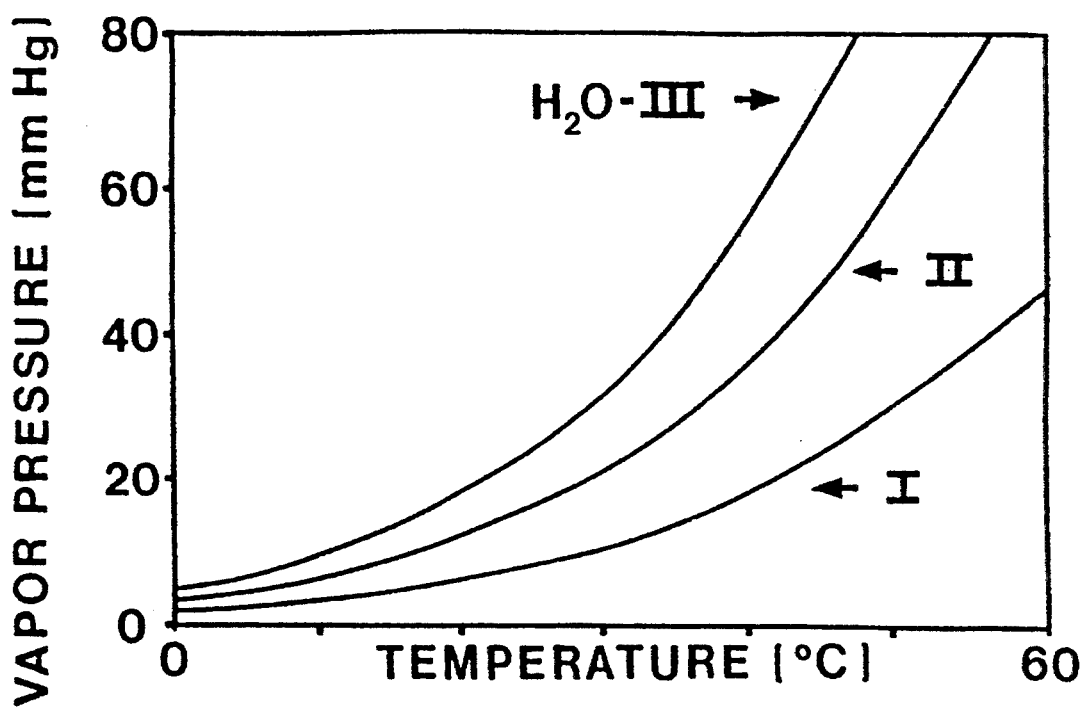
FIG. 2 shows typical vapor pressure temperature curves for water and hydrates of a salt, MA.

FIG. 2 shows the effect of temperature on the equilibrium of the system described above. On each line the phases stable in the adjacent regions are in equilibrium. The stable crystal or liquid phases are: Below I, anhydrous; I-II, MA.sH$_2$O; II-III, solution.

As noted earlier, the sensors of this technology undergo both optical and dielectric constant changes of great potential utility. These changes may be utilized separately or together. Utilizing optical changes only will be considered first. As noted, this technology uses sensing pounds which undergo isotropic/anisotropic changes at the phase shift point or "trigger" point. In the isotropic form the optical properties of the solution are the same in every direction. The phase shift forms anisotropic crystals which have optical properties which vary with direction. In particular, the crystals have at least two indices of refraction and so are birefringent. Further, the shift from the clarity of the liquid phase to the opalescence of the crystal phase may be amplified readily with polarizers.

Figure 3:
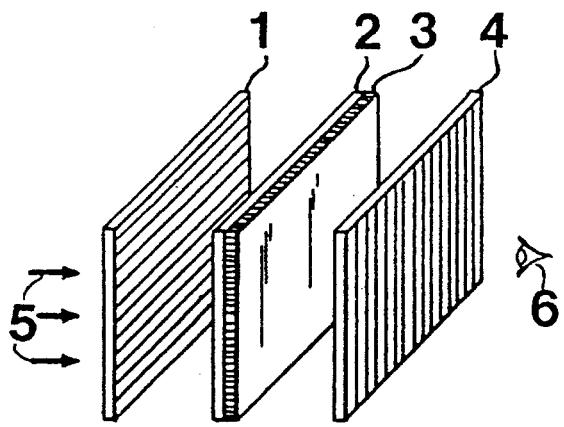
FIG. 3 is a schematic view of an optical-type transmission system.

In a representative transmission-type embodiment of the optical mode of the present invention shown in FIG. 3, a light beam from light source 5 which may be a window, a tungsten lamp, an LED, etc. passes through polarizer 1 where the light beam is polarized. The beam then passes through transparent or translucent substrate 2 which may be glass or some isotropic plastic such as cellulose triacetate, on which is deposited sensor layer 3. The beam passing through 2 and 3 then encounters analyzer 4 whose polarizing axis is usually at right angles to the polarizing axis of 1 so as to result in what is generally termed "dark field."

If the coating 3 on substrate 2 is in its nonbirefringent mode, little light passes through analyzer 4 and the system appears "dark field" to viewer 6. However, if the humidity changes sufficiently, coating 3 becomes birefringent. When a light beam enters a birefringent or, as it it is sometimes called, double refracting material, it is divided into two components, one defined as an extraordinary ray and the other as an ordinary ray, each vibrating in a direction at right angles to the other and traversing the birefringent material with a different velocity to thereby introduce a phase difference there between. As said beam is thereby resolved into two components, one of which is retarded with respect to the other, said beam is generally referred to as being elliptically polarized. The two components emerging from the birefringent material and entering the second sheet of polarizing material 4 are resolved into one plane-polarized beam again. But a phase difference has been introduced between the two parts of this same beam, and so the necessary conditions for interference are present. With a white light source brilliant colors will emerge from analyzer 4 if the coating consists of large crystals. However, when the crystals are very small there is a mixing of colors and the crystal mass appears white. But in either case the field which was previously a blueblack passing very little light now glows brilliantly.

Figure 4:
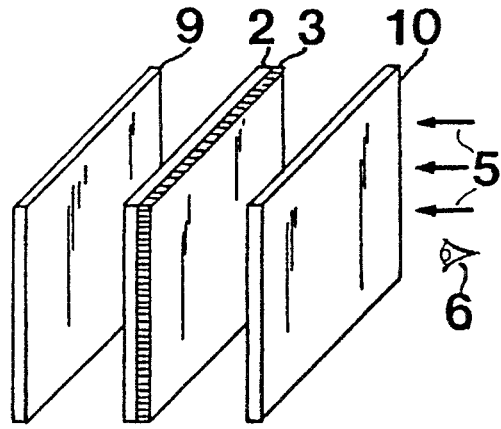
FIG. 4 is a schematic view of an optical-type reflection system.

FIG. 4 typifies a reflection-type system in which light beams from a source 5 pass through a circular-type polarizer 10 where they are circularly polarized. They then pass through the sensor layer 3 coated onto substrate 2 to the polarization conserving mirror 9. When the coating 3 is non-birefringent, no light will be reflected back through 10 because the circular polarizer has polarized the beam to a "right-handed" or "left-handed" helix form which cannot pass back through the circular polarizer 10. When coating 3 becomes birefringent, the polarization form of the light that is reflected from the mirror is altered and the returning light passes through the polarizer 10.

Figure 5:
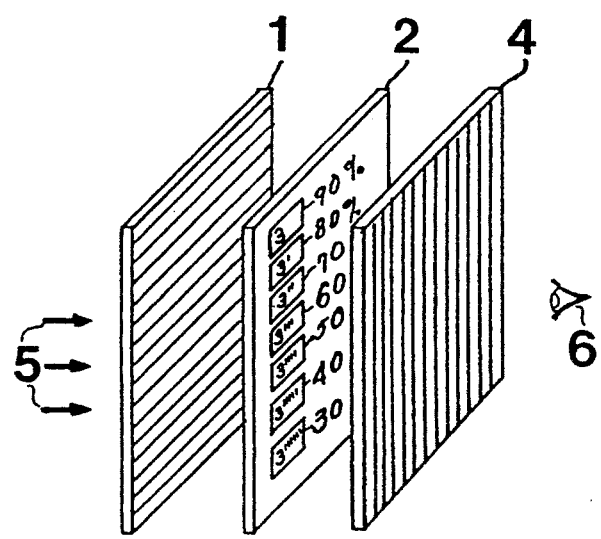
FIG. 5 is a schematic view of an optical-type transmission system using sequential RH series plaques.

FIG. 5 also represents a transmission-type embodiment of the optical mode but it is one in which a graded series of RH sensors are displayed so as to cover a particular humidity range. It is similar to FIG. 3 but instead of a single coating 3 on substrate 2, the graded series 3, 3' 3", etc. are applied in discrete areas on the substrate.

Figure 6:
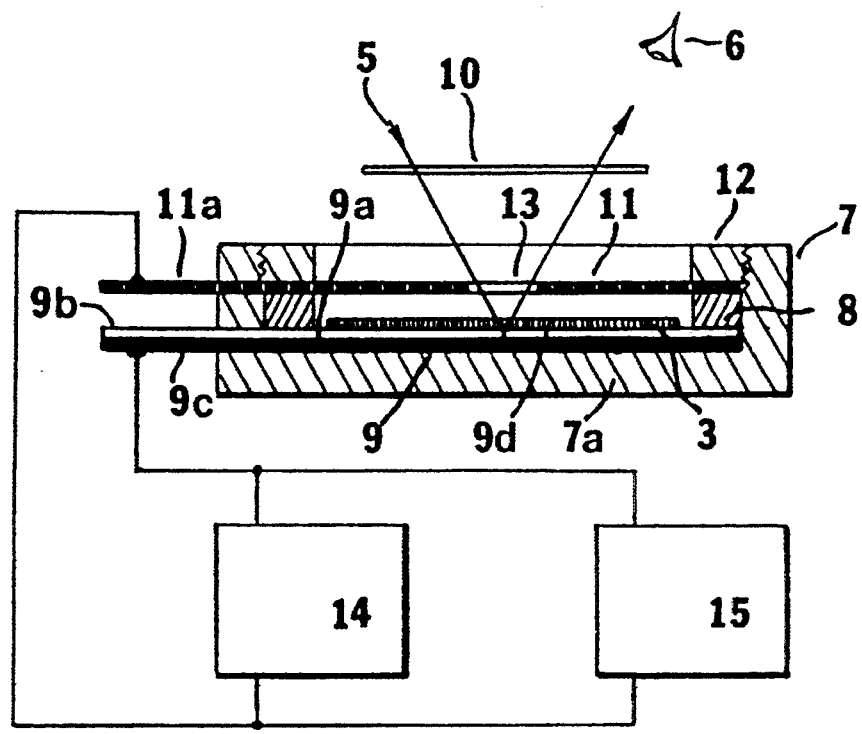
FIG. 6 is a section of a capacitance-type humidity sensing device.

FIG. 6 represents a section of a typical embodiment of the capacitance/optical mode of the technology. 7 is a side slotted, annular holder made of an electrically insulating polymer of low water sorption character such as Teflon into which a threaded retaining ring of Teflon 12 screws. 9 is a flat, polished circular metal mirror electrode coated on the upper mirror side 9a with a thin, istropic electrically insulating film such as the insulating polymer heretofore referred to or an aluminum oxide as is identified in FIG. 6 at 9b placed upon the base 7a of holder 7 and which has a long narrow tab 9c extending through the side of slotted holder 7. 3 is a humidity-responsive sensor coating of the present invention coated on the middle of the upper surface 9d of mirror 9. 8 is an annular spacing ring of an electrically insulating, low water sorption polymer such as Teflon machined to a precise thickness. 11 is a flat, perforated, circular, metal electrode having a long, narrow tab 1 1 a (similar to that of 9) which extends through the side of the slotted holder 7. To monitor the state of the sensor film, a light beam from light source 5 passes through circular-type polarizer 10 where the beam is circularly polarized. Then the beam passes through the circular aperture 13 in perforated metal electrode 11 and then, as in FIG. 4, through the sensor layer 3 coated onto mirror substrate 9. As explained before, reflected light from light mirror 9 emerges from the aperture 13 and passes through the polarizer 10 to be perceived by the viewer or by a photoresponsive device at the moment the sensor layer 3 becomes birefringent. Electrodes 9 and 11, of course, are connected to a suitable capacitance meter 14 which may be calibrated in percent RH rather than picofarads. Voltage is applied to the electrodes by voltage source 15. Prior determination of the primary, inherent "trigger point" or optical phase change point of the sensor material used allows precise checking against the readout shown by the capacitance meter at the moment of optical shift. Perforated electrode 11 may have its viewing port and ventilation holes closed with a very thin coating of a polymer highly permeable to water vapor (such as cellulose acetate butyrate) if it is desired that the cell be impermeable to liquid water. In such a case the emerging electrode tabs are sealed with an RTV silicone compound. A polymer coating 0.002 mm. or less is suitable on the top electrode.

Figure 7:
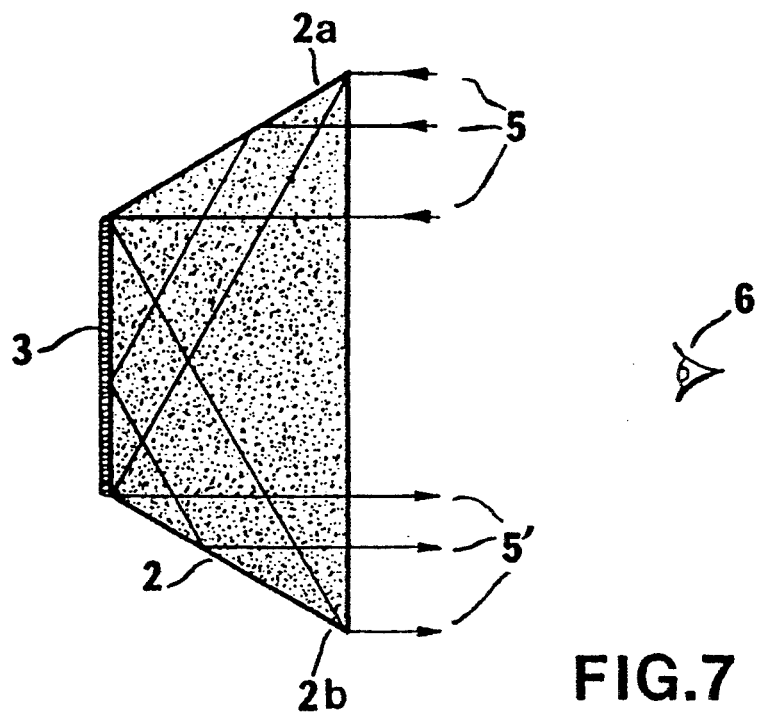
FIG. 7 is a section of an optical-type reflection system not requiring polarization amplification.

FIG. 7 is a cross section of a trapezoid-shaped bar of transparent glass or of a plastic such as polymethyl methacrylate. This has been discovered to generate excellent optical signals without the use of polarizer amplifiers when used with the humidity sensors of the present invention. The device consists of a bar shaped substrate 2 of suitable length to carry one or more plaques of sensor coating 3 on its back side. Light beams from light source 5 enter the trapezoidally shaped bar whose angles have been chosen to cause total reflection to occur to the beams which encounter the two non-parallel sides 2a, 2b of the trapezoid. To illustrate this reflection, beams 5 are shown entering the structure, being internally reflected, and exiting as beam 5'. Since the trapezoid is symmetrical, this reflection occurs on both sides.

Unexpectedly, the sensors of the present invention have been found to optically couple with the trapezoidally-shaped substrate when the sensors are in their birefringent, opalescent phase. The viewer 6 perceives only a faint, opalescence when looking through the bar 2 and the coating 3 in the center zone (between the lines of beams 5 and 5'). However, the two edge zones, which are mirror reflections of coating 3, appear brilliantly white. When sensor coating 3 shifts to isotropic and transparent, the two edge zones reflecting that sensor abruptly become silver, giving a dramatic signal shift.

Many variations of this structure are possible. The front center zone can be used to carry a scale showing the trigger humidities of a graded series of sensor plaques on the back side. Instead of a trapezoidal shape, a semicircular or even half of an annular shape can be used. In the case of the trapezoidal shapes, it is necessary to select trapezoid angles which will cause total internal reflection within the particular transparent material used. The "critical angle" can be readily calculated from the index of refraction of the desired substrate, of course. Light beams also can be passed into either end of such bars to illuminate sensors coated on the back. If desired, the readout from these systems can be further enhanced by viewing the front face through a circular-type polarizer parallel with it.

If a trapezoidal shape is used, the humidity-sensing compositions are applied only to the flat back of the device, in one or more stripes of any desirable width, optimally extending from one edge to the other whatever the width selected for the back of the trapezoid. Though such stripes can be carried up the non-parallel sides of the trapezoid, only a very small increase in signal contrast results and the effort is not warranted.

If a semicircular or semiannular shape is coated with one or more humidity-sensing compositions, the stripes as before are parallel and of any convenient width. For convenience in coating, the stripes may extend from one front edge to the other front edge, spanning the entire 180° of the semicircle. However, the length of the stripe may be substantially shortened while still generating a good optical signal. Generally, it is desirable that at least 25% of the semicircular arc be coated and the coating should be of approximately equal length either side of the centerline.

FIG. 8a is a capacitance vs. RH curve of a sodium/potassium mixed crystal salt complex such as is described in claim 13 of my U.S. Pat. No. 4,166,891. It has an optical trigger point of 50% RH (indicated by the vertical dashed line at 50%). Magnesium compounds are an essential stabilizing component in this complex of the alkali metal salts of 3,3',4,4' benzophenonetetracarboxylic acid. As noted elsewhere, magnesium compounds cannot be used in conjunction with the complexing of the alkali metal organic salts of the present invention since they cause decomposition. The huge shift in the dielectric constant of the complex, as indicated by the almost vertical shape of the capacitance vs. RH curve, occurs concurrently at the optical trigger point. This curve was developed using the sensor fixture illustrated in FIG. 6, as were the other curves shown in the FIG. 8 series.

FIG. 8b is a capacitance vs RH curve of the pure organic salt cesium benzoylpropionate, whose operation is described in detail further on. In this typical example, the large, linear change in the dielectric constant extends over almost five decades of relative humidity as indicated by the vertical, dashed lines. Homologs of this compound extend the range covered to very high humidities and lattice modifiers extend the range to very low humidities. As noted elsewhere, the optical shift for each compound occurs at a very precise humidity along its capacitance vs. humidity curve.

FIG. 8c shows capacitance vs. RH curves of the inorganic salt, calcium chloride, compounded with a high surface area silica. As a matter of interest, curve 1 shows both the high RH as well as the low RH portions of the curve. However, as explained in detail further on, this sensor is an example of a special type used for monitoring low humidities under very rigorous conditions. Thus, curve 2, which is a capacitance vs. RH curve developed with the identical sensor after a 500° C. thermal processing, was tested only at lower humidities since this is the range of interest.

The vertical dashed line marks the 2000 parts per million by volume of water vapor which the Military has established as the limit of internal water vapor content for high reliability microcircuits packaged in hermetically sealed ceramic packages. This is equivalent to approximately 8% RH at 20° C. and it is in this lower range that a sensor such as this is used for monitoring the atmosphere of sealed packages.

FIG. 8d shows the same two capacitances vs. RH curves 1 and 2 as shown in FIG. 8c, but the scales are expanded to cover only the capacitance and RH ranges of interest. It shows the capacitance readouts which can be readily secured in greater detail then can be seen in the curves of FIG. 8c.

Curves 1 and 2, FIG. 8d, vary by about 1.5% RH since, as explained elsewhere, the test assembly shown in FIG. 6 was not designed to be fired at 500° C. In particular, after developing curve 1, the assembly was disassembled, the electrode bearing the Sensor film was fired at 500° C., cooled, and reinstalled in the assembly for determining curve 2. Capacitance test devices designed to be assembled and disassembled are manufactured to very close tolerance because of the large change in capacitance with small change in electrode clearance. The test device of FIG. 6 is not of this precision. However, the FIG. 6 device, once assembled, has repetitively generated such curves as are shown in FIG. 8a and FIG. 8b. Curves such as 1 and 2 of FIG. 8c and FIG. 8d, though already acceptable by present commercial standards, are expected to fall into very close clusters when sensors such as are described here are installed in electrode assemblies designed for high temperature processing.

Turning to the chemical compounds which I have discovered exhibit these concurrent optical and dielectric constant changes, I have found them remarkable for their sensitivity to very small changes in the humidity of gases in contact with them. This is believed to be due to the unusually propitious balance of forces within the molecules. Thus, as the ambient humidity varies and they shift phase from an isotropic solution to anisotropic crystals, they do not form the highly organized, tightly bound type of crystal which dissolves with difficulty as the humidity varies. Nevertheless, the intermolecular forces among the dissolved molecules are strong enough to eliminate any tendency toward supersaturation when water leaves the system.

There is an explanation for this remarkable behavior. Though I do not wish to be bound by theory, it is believed that the salts of the present invention form lyotropic liquid crystals as solvent water leaves their isotropic solutions. Though a good deal of work has been done on "thermotropic" liquid crystals (the type used in "liquid crystal" thermometers and electronic "liquid crystal" displays) and which are entirely different, little work has been done with lyotropic liquid crystals. The common bond between the two categories is that in each case the sensing molecules shift between an isotropic liquid state and a "liquid crystal" state. The term "liquid crystal" is used to describe a state in which a good deal of molecular order is present as compared with the liquid state. However, the molecules are not as organized as they are in the solid where constituent molecules execute small vibrations about firmly fixed lattice positions but cannot rotate. The ordinary liquid state, of course, is characterized by relatively unhindered molecular rotation and no long-range order.

First turning to the chemistry of these sensors in a general way, the sensory molecules are amphiphilic. That is, they are characterized by possessing an organic ring structure-that is water insoluble (hydrophobic) and a side chain with a polar head (ionic) which dissolves readily in water (hydrophilic). However, I theorize that under suitable conditions the cation of the side chain bonds to the oxygen of the benzoyl group to form a novel polar ring complex which is highly susceptible to hydration because of its ionic nature. This compact multi-ring structure which forms is believed to be unusually suitable for the formation of lyotropic liquid crystals. It is also a structure offering excellent stability to heat and ultraviolet light.

I have found that a number of molecular structural modifications can be made and still preserve the essential humidity-response of the sensors of the present invention. However, the alkali metal salts of 3-benzoyl-propionic acid, $C_6H_5COCH_2CH_2CO_2H$, or the alkali metal salts of the ring-substituted benzolypropionic acids have proven of exceptional utility. The alkali metals which are useful include lithium, sodium, potassium, rubidium, and cesium since the different metals form salts which trigger or undergo phase shifts at different humidities. Further, so as to prepare formulations which trigger at intermediate humidities, mixtures or so-called mixed crystals can be formed by cross-mixing the salts of the different alkali metals.

Among the various substituent groups which are useful in modifying the phenyl ring, I have found that alkyl groups create compounds whose alkali metal salts trigger at humidities far higher than do those of the non-alkylated benzoylpropionic acid. For example, the compounded potassium salt of 3-benzoylpropionic acid triggers at about 53% RH at 20° C. but the compounded potassium salt of 3-(4-ethylbenzoyl) propionic acid, $C_2H_5C_6H_4COCH_2CH_2CO_2H$, triggers at 83% RH at 20° C. A greater degree of alkylation raises the trigger point of the alkali metal salts still higher.

The lowest humidity which the compounded (but nonmodified) alkali metal salts of 3-benzoylpropionic acid will sense is 35% RH at 20° C., the trigger point of the cesium salt. However, it is desirable to sense much lower humidities. I have discovered a new class of compounds which meet this need, and I term them "lattice modifiers" since they are believed to function by profoundly altering the intermolecular forces within the liquid crystal lattice. Thus, the prime, sensing molecules (for example those of cesium benzoylpropionate) do not associate at their "natural" trigger humidities but at much lower humidities when mixed with these lattice modifiers.

These modifiers are chain-like with polar heads (ionic) and they closely resemble the side chain attached to the phenyl group of prime sensing salts such as cesium benzoylpropionate, $C_6H_5COCH_2CH_2CO_2Cs$, in which —$COCH_2CH_2CO_2Cs$ is the side chain. For example, am effective lattice modifier, cesium hydroxybutyrate, $H_2COHCH_2CH_2CO_2Cs$, is the same as cesium benzoylpropionate's side chain except that the keto group ($C=O$) has been replaced by an hydroxyl group (C—OH). As before, it is believed that the chain forms a ring structure in which the Cs bonds to the oxygen of the hydroxyl group. It is theorized that these molecular "separators" or spacers make it increasingly difficult for the prime sensing molecules to assemble into liquid crystal signalling "swarms" or arrays. The reduction of the RH trigger point is a linear function of the quantity of lattice modifier added, and the modifiers are quite potent. By such a method the trigger point can be reduced below 15% RH at 20° C. while preserving the full brilliance of readout and the sensitivity to small humidity changes.

What I term "compounding" of the prime sensor salts and their lattice modifiers is also of great value, though for many applications the sensor salts (with or without modifiers) can be used as uncompounded solutions. When they are used in an uncompounded form, it is desirable to limit the area and depth of each incremental sensor salt deposit so that surface tension prevents running or draining of the deliquesced liquid which it forms at high relative humidities. This is especially true if the sensors are to be used in the vertical position. Then the solution can be applied in small droplets. If desired, the surface tension of the substrate area between droplets can be readily raised by crosshatching the substrate with narrow line deposits of water repellent materials such as fluoropolymers.

Compounding of the sensor salts offers various benefits. For example, equalizing the viscosity and surface tension of 16 or more sensor solutions before simultaneously coating a graded RH series onto a moving substrate greatly facilitates the process. Once ,applied, proper compounding creates chemical complexes which signal brilliantly, shifting from a birefringent liquid crystal state to an isotropic gelled state, a form which never becomes fluid enough to drip or run at high humidities.

In my U.S. Pat. No. 4,166,891 I describe polymers and certain metals and borates which create complexes of great utility when used with those chemical sensors. In the claims covering those complexes I particularly specify magnesium, $Mg^{++}$, because it is essential to the long term stability of those complexes. However, I have discovered that the chemistry of the present sensor compounds is entirely different from that encountered with the alkali salts of 3,3'4,4' benzophenone tetracarboxylate, the sensors of the earlier invention. With the new sensors the inclusion of magnesium salts brings immediate formation of insoluble complexes which make the composition useless. Thus, though there appear to be similarities between the complexing of the benzophenone sensors and the salts of the present invention, the essential chemistry of the complexing is entirely different as is confirmed by the magnesium reaction.

As before, I have found that water soluble, organic polymers containing repetitive oxygen-bearing groups including the hydroxyl, the carboxyl, the sulfonic acid group, or mixtures of them repetitively present along a substantially linear chain are useful compounding ingredients. Examples of these polymers, which are preferably solid and which have proven effective, are as follows: carboxyl group—poly(methyl vinyl ether/maleic anhydride), poly(styrene/maleic anhydride), polyacrylic acid; sulfonic acid group—polyvinyl sulfonic acid; methoxy group—methoxy cellulose; polyether group—polyethylene oxide; polyamide group poly(-vinylpyrrolidone). The carboxyl and sulfonic acid groups must be neutralized with an appropriate alkali metal compound before use so that the system is neutral or slightly basic. Some of these polymers are modified in various ways during manufacture. For example, polyacrylic acid is often modified by inclusion of methacrylic acid and/or crosslinking agents during manufacture.

The molecular weights of the polymers in general are not critical so long as the polymers form stable, water solutions of appropriate viscosity. Usually, from about 2% to 8% of the polymer in a coating solution containing 8% by weight of sensor salt contributes good rheological properties to the coating solution.

Though I do not wish to be bound by theory, it is thought that the metal cations which I have found effective with the present chemical sensors coordinate with the oxygen of the polymers to form elaborate network structures. The metal ions which coordinate with the polymers and with the sensors of the new invention to form appropriately complexed compositions are $Cu^{++}$, $Ni^{++}$, $CO^{++}$, $Mn^{++}$, $Al^{+++}$, $Zn^{++}$, and $Cr^{+++}$. Since the salts must be appropriately soluble for reaction, the nitrate, chloride, acetate,and sulfate typify useful anions. Usually about 5 tool percent of the metals present in an alkali metal benzoylpropionate/polyvalent metal salt mixture must be of the polyvalent metal salt for good complexing, though as little as 0.4 mol percent may prove adequate.

Besides the heavy metal cations which form such useful networks with the polymers to enhance viscosity in the solution and in the deliquesced film, I have found that the boron introduced as a borate is a most effective agent to gel the viscous films which form on evaporation of water from a sensor salt/polymer/polyvalent heavy metal salt solution. Alkali metal borates form complex ring structures in water, and it is believed that the oxygenated polymers and polyvalent cations react with these rings to form elaborate stable networks which can readily swell at high humidities but which are so crosslinked that they cannot dissolve.

I have found that about two mol percent of borate ion on the basis of the metals present in the sensor salts/-polyvalent metal salts/polymers blend usually prevents any dripping even at 90% RH and 50° C. However, as little as 0.25 tool percent can prove adequate and as much as 10 mol percent can prove desirable when very high humidities are expected. The strength of the complexing of these components, namely, the alkali metal sensor salts and borates, the heavy metal salts, and the polymers is demonstrated by the brilliantly clear solutions which form while at the same time the nonflowing films which they form retain their integrity at high temperatures and humidities.

Finely divided inorganic compounds having little or no birefringence and possessing a high surface area also can be used advantageously in compounding the prime sensor salts and their lattice and modifiers. Since the dielectric constants of the inorganic compounds are quite different from those of organic polymers which are also most useful in compounding, they offer a ,host convenient mode of modifying the electrical characteristics of the sensor system while securing rheological properties in the sensor solutions which make them suitable for successful coating.

Precipitated and pyrogenic silica, diatomaceous earth, and pyrogenic aluminum oxide typify oxides which are commercially available having surface areas as high as 50–200 sq. meters/gram. From 0.5 to 4.0% by weight of such materials can be readily dispersed in aqueous solutions of prime sensor salts (containing lattice modifiers where desired) which contain from 10–50% of sensor salts by weight. The pH of the suspension is then adjusted to the 7.5–8.5 range using the appropriate alkali metal hydroxide. Such dispersions coat well and dry to films of great sensitivity to humidity changes and free of drainage problems.

Pyrogenic aluminum oxide and silica are of exceptional value because by empirically adjusting the ratio of one oxide to the other the viscosity of a particular dispersion can be adjusted over a much wider range than can be secured with either alone.

I have found that there is still another type of compounding component which is essential for good signalling with lyotropic liquid crystals. I term such materials "lattice stabilizers, and they stabilize the liquid so that the liquid crystals form but one type of structure. Solid crystals often can form more than one well-defined structure, and so there is often a problem with stabilizing a system so that only the desired crystal type forms. Liquid crystals, however, are much more complex since the intermolecular bonds are weaker. Thus, many subtle, undesirable variations on a particular, desired crystal structure can occur in an uncontrolled system because of temperature variations, variations in the rate of crystal formations etc. However, I have discovered certain additives which are believed to create a kind of "reference lattice structure" within the lyotropic liquid crystal system so that the sensor molecules always assemble into crystals in such a way as to generate the same optical and dielectric constant readouts. This reference lattice structure is invisible but potent in its organizing power.

One type of lattice stabilizer consists of aryl hydrocarbons of low vapor pressure which dissolve in the sensor salt/polymer/water system to form organizing complexes of still lower vapor pressure. Examples of hydrocarbons which perform well include Monsanto's HB40, which is a partially hydrogenated terphenyl which also contains about 40% of terphenyl. 1,1-di(ortho-xylyl)ethane, 1,2,3, 4 tetramethylbenzene, 1,2,4,5 tetramethylbenzene, 1,2,3,5 tetramethylbenzene, 1,2,3,4,5 pentamethylbenzene, and cyclohexylbezene are also hydrocarbons which bring about consistent organization of the liquid crystals, increase the brightness of optical readout, and minimize hysteresis. Hysteresis is the difference in the humidity level at which triggering occurs when the humidity is rising compared to that met when the humidity is falling. Typically, from 1 to 3% of the hydrocarbon on the basis of contained solids is very effective.

Another type of potent lattice stabilizer consists of certain surface active agents in which a stable fluorocarbon tail, $F_3C(CF_2CF_2 \ldots)$ is attached to a water-solubilizing group, X. The alkali metal perfluoroalkyl sulfonates, carboxylates, and acid phosphates comprise the compounds which are effective. The perfluoroalkyl group varies in length among different compounds and manufacturers but typically includes 3 to 8 carbons. A small concentration of agent is usually quite effective. From 0.1% to 0.3% on the basis of contained solids is usually quite effective.

Having overviewed the various components of these complex but remarkably effective and useful systems, it is helpful to consider the components in greater detail. Since the salts of benzoylpropionic acid and its homologs and analogs comprise the central sensors of these systems, the synthesis of benzoylpropionic acid is most useful to consider. Typically, the various acids from which effective sensor salts can be made can be synthesized by using the same method or a variation on the method which would be obvious to one skilled in the art. Usually, a variation in concentration of reactants, temperature of reaction, or choice of solvent will produce a satisfactory yield of the desired acid in good purity.

The Friedel and Crafts reaction is the one most useful for preparation. The reaction of succinic anhydride with benzene or the desired alkylated or arylated benzene or substituted benzene in the presence of anhydrous aluminum chloride produces the desired aroyl acid in good yield and purity. More generally, the Friedel and Crafts reaction between an aliphatic dibasic acid anhydride and an aromatic compound results in the formation of an aroyl fatty acid with the aroyl group situated at the last carbon atom of the aliphatic chain.

PREPARATION OF BENZOYLPROPIONIC ACID

In a 2-1, three-necked, round-bottomed flask fitted with a mechanical stirrer and two reflux condensers are placed 68 g. (0.68 mole) of succinic anhydride and 350 g. (4.5 moles) of dry, thiophene-free benzene. The stirrer is started, and 200 g. (1.5 moles) of powdered, anhydrous aluminum chloride is added all at once. Hydrogen chloride is evolved and the mixture becomes hot. It is heated in an oil bath and refluxed, with continued stirring, for half an hour. The flask is then surrounded by cold water, and 300 cc. of water is slowly added from a dropping funnel inserted in the top of one of the condensers.

After the addition of water to the aluminum chloride complex, 100 cc. of concentrated hydrochloric acid (sp. gr. 1.18) is added and the benzene is removed by steam distillation. The hot mixture is transferred to a 1-l. beaker, and the 3-benzolypropionic acid separates as a colorless oil which soon solidifies. After cooling to 0° C. it is collected, washed with a cold mixture of 50 cc. of concentrated hydrochloric acid and 150 cc. of water, and then with 200 cc. of cold water. The crude acid is dissolved in a solution of 75 g. of anhydrous sodium carbonate in 500 cc. of water by boiling for fifteen minutes. The solution is filtered with suction and the small amount of aluminum hydroxide washed twice with 50-cc. portions of hot water. Four grams of charcoal is added to the hot filtrate; the solution is stirred for three to four minutes and then filtered with suction. The clear, colorless filtrate is transferred to a 2-l beaker, cooled to $50+\cong 60°$ C., and carefully acidified with 130 cc. of concentrated hydrochloric acid. After cooling to 0° C. in an ice-salt bath the acid is filtered, washed well with water, dried overnight at room temperature, and finally dried to constant weight at 40°–50° C. The yield is 110–115 g. (92–95 percent of the theoretical amount). It melts at 114°–115° C. and needs no further purification.

Among the more important homologs of 3-benzylpropionic acid which I have prepared are the following acids and (in parenthesis) the hydrocarbons frown which they were prepared:

| | |
|---|---|
| 3-(4-methylbenzoyl)propionic acid | (toluene) |
| 3-(4-ethylbenzoyl)propionic acid | (ethylbenzene) |
| 3-(4-propylbenzoyl)propionic acid | (propylbenzene) |
| 3-(4-isopropylbenzoyl)propionic acid | (cumene) |
| 3-(4-butylbenzoyl)propionic acid | (butylbenzene) |
| 3-(4-amylbenzoyl)propionic acid | (amylbenzene) |
| 3-(3,4-dimethylbenzoyl)propionic acid | (o-xylene) |
| 3-(2,4-dimethylbenzoyl)propionic acid | (m-xylene) |
| 3-(2,5-dimethylbenzoyl)propionic acid | (p-xylene) |
| 3-(2,4,6-trimethylbenzoyl)propionic acid | (mesitylene) |
| 3-(2,3,4,5-tetramethyl-benzoyl)propionic acid | (1,2,3,4, tetra-methylbenzene) |
| 3-(2,3,5,6-tetramethyl-benzoyl)propionic acid | (1,2,4,5 tetra-methylbenzene) |
| 3-(2,3,4,5,6-pentamethyl-benzoyl)propionic acid | (pentamethyl-benzene) |
| 3-(4-phenylbenzoyl)propionic acid | (biphenyl) |
| 3-(4-cyclohexylbenzoyl)propionic acid | (cyclohexyl-benzene) |

Among the substituted benzoylpropionic acids which I have used to prepare various salts are 3-(4-bromobenzoyl) propionic acid , 3-(4-fluorobenzoyl) propionic acid, 3-(4-chlorobenzoyl) propionic acid, and 3-(4-methoxybenzoyl) propionic acid It is thought that the alkali metal salts of benzoylpropionic acid form a 7-member ring structure in which the alkali metal cation binds to the keto group. By varying the length of the aliphatic chain from the three carbons of the propionic chain, various size rings are believed to be formed. Various size rings are known to be stressed in varying ways depending on the number, type and position of atoms forming the ring. Usually, the ring with minimal stress is the most stable. In the case of the sensors of present invention, in general the 7-member ring formed by the alkali metal benzoylpropionates is most stable and signals best.

So as to arrive at the most stable and most effective sensors, the salts of acids possessing chains of varying length have been evaluated. Among these acids 4-benzoylbutyric acid, $C_6H_5CO(CH_2)_3CO_2H$ benzoylformic acid, $C_6C_5COCO_2H$ and of course 3-benzoylpropionic acid are most useful for preparing humidity-sensing salts for standard applications. Acids having longer chain lengths are suitable for specialized sensor salts.

Introducing other elements in place of carbon in a ring structure is known to also affect the stresses in the ring Thus, I have investigated the salts of analogs of benzoylpropionic acid in which, for example, nitrogen has replaced carbon. A good example of this is hippuric acid, $C_6H_5CONHCH_2CO_2H$ in which the NH replaces one of the $CH_2$ groups of the propionic acid chain. 4-nitrohippuric acid, $O_2NC_6H_4CONHCH_2CO_2H$ has also been examined. Other compounds of this type but of differing chain lengths, so that rings of varying size are believed to form, include the following:

N-benzoyl-B-adenine $C_6H_5CONHCH_2CH_2CO_2H$
N-(4-aminobenzoyl)-B-alanine $H_2NC_6H_4CONHCH_2CH_2CO_2H$
N-(4-nitrobenzoyl)-B-alanine $O_2NC_6H_5C_6H_4CONHCH_2CH_2CO_2H$
N-(p-nitrobenzoyl)-6-aminocaproic acid, $O_2NC_6H_4CONH(CH_2)_5CO_2H$ Instead of single rings such as are present in benzene or biphenyl, fused rings such as are found in naphthalene can be reacted in form aroyl compounds. Additional compounds whose salts have been evaluated include the following:

gamma-oxo-1-naphthalenebutyric acid, $C_{10}H_7COCH_2CH_2CO_2H$
gamma-oxo-2-naphthalenebutyric acid, $C_{10}H_7COCH_2CH_2CO_2H$
gamma-oxo-1-pyrenebutyric acid, $C_{16}H_9COCH_2CH_2CO_2H$ The study of the physical chemistry of the lattice modifiers which I have discussed before also has added greatly to an understanding of these systems. That is because, as I have already noted, the modifiers closely resemble the side chains attached to the aryl groups of the prime sensing salts. It is believed that the chain of the modifier forms a ring structure in which an alkali metal carbon bonds to an equivalent of the keto group of benzoyl propionic acid. Because of their structural similarity, discoveries in one system assist in the understanding of the other.

Among the acids which have been evaluated as 6-member formers are malonic acid, $HO_2CCH_2CO_2H$, and tartronic acid, $HO_2CCH(OH)CO_2H$. Acids whose salts were investigated and which form 7-member rings include the following:

succinic acid, $HO_2CCH_2CH_2CO_2H$
levulinic acid, CHhd 3$COCH_2CH_2CO_2H$
ketoglutaric acid, $HO_2CCH_2CH_2COCO_2H$
hydroxybutyric acid, $HOCH_2CH_2CH_2CO_2H$
succinamic acid, $H_2NCOCH_2CH_2CO_2H$
aminobutyric acid, $H_2N(CH_2)_3CO_2H$ Acids whose salts were worked with arid which may form 8-member rings are glutaric acid, $HO_2C(CH_2)_3CO_2H$, and its fluorinated derivative, perfluoroglutaric acid, $HO_2C(CH_2)_3CO_2H$. A possible 9-member ring forming salt examined is that of aminocaproic acid, $H_2N(CH_2)_5CO_2H$.

The alkali metal salts of analogs of these same acids, in which a phenyl group replaces a hydrogen of one of the methylene groups, also work well as lattice modifiers. Examples of acids useful for preparing effective lattice modifiers of this type include the following phenylsuccinic acid, phenylmalonic acid, phenylhydroxybutyric acid, and phenylglutaric acid.

From these interrelated studies has been developed a general formula for the acids which form the anions of these humidity sensors:

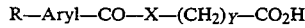

R—Aryl—CO—X—$(CH_2)_Y$—$CO_2H$ where
R is hydrogen, halogen, alkyl, alkoxy, or a nitro group.
Aryl is phenyl or a connected ring structure such as a biphenyl or a fused ring structure such as naphthalene, acenaphthene, fluorene, anthracene, or pyrene.
X is a nitrogen or a carbon attached to the adjacent methylene with either a single or double bond.
Y is 0 to 7

In a similar way, there has been developed a general formula for the acids whose alkali metal salts comprise the lattice modifiers which allow a smooth and essential reduction of the trigger humidities of the prime sensor salts:

R—CZ—$(CH_2)_Y$—$CO_2H$ where

R is amino, hydroxyl, carboxyl, or a methyl group.
Z is hydrogen, hydroxyl, or a keto group.
Y is 0 to 4.

I have already given information on the synthesis of the acids which are reacted to form the sensing salts of technology. The preparation of two typical alkali metal salts useful as humidity sensors in the pure state or as components of compounded materials follows:

PREPARATION OF CESIUM BENZOYLPROPIONATE 72.0 g. of 99% pure 3-benzoylpropionic acid is slurried in 100 cc. distilled water. 97.3 g. of a 4.11 molar, pure cesium hydroxide solution is added and the temperature raised to 65° C. to obtain complete solution. The solution is filtered through No. 40 filter paper to remove dust, etc. The solution is then evaporated on a hot plate to 200 g., which gives a 2 molar concentration, and it is then bottled.

PREPARATION OF POTASSIUM ETHYLBENZOYLPROPIONATE 83.3 g. of 99% pure 3-(4-ethylbenzoyl) proponic acid is slurred in 100 cc. distilled water. 49.1 g. of 8.144 molar, pure potassium hydroxide solution is added and the temperature is raised to 65° C. to obtain complete solution. The solution is filtered through No. 40 filter paper to remove dust, etc. The solution is then evaporated on a hot plate to 200 g., which gives a 2 molar concentration, and it is then bottled.

The preparation of the salts which I have termed lattice modifiers is equally straightforward.

PREPARATION OF CESIUM LEVULINATE 46.9 gr. of 99% pure levulinic acid is sluurried in 100 cc. distilled water. 97.3 g. of a 4.22 molar, pure cesium hydroxide solution is added and the temperature is raised to 65° C. to obtain complete solution. The solution is filtered through No. 40 filter paper to remove dust, etc. The solution is then evaporated on a hot plate to 200 g., which gives a 2 molar concentration, and it is then bottled. These materials are readily compounded into highly stable solutions which can be readily coated onto a variety of substrates. The preparation of a sensor solution of cesium benzoylpropionate, which triggers optically at 35% RH at 20° C. (when applied as a film); typifies the preparation of sensors useful for lower RH sensing.

PREPARATION OF A 35% RH SALT SOLUTION

The following materials are weighed together:
120 g. 10% cesium polyacrylate solution
338 g. distilled water
30 g. M/40 zinc acetate solution
12 g. 4% cesium borate
100 g. 2M cesium 3-benzoylpropionate
1 g. Monsanto's HB40

Slow speed agitation serves nicely to mix the various major ingredients. However, the HB40 must be dispensed using a high speed mixer.

By dissolving into the compounded sensor salt increasing quantities of a lattice modifier such as cesium levulinate, whose preparation has been described before, the trigger point of the blend can be smoothly and linearly reduced to 15% or less.

The preparation of a sensor solution of potassium 3-(4-ethylbenzoyl) propionate, which triggers at 83% RH at 20° C. (when applied as a film) is representative of the preparation of sensors which trigger at higher humidities. The procedure is essentially the same as that described for the 35% RH sensor salt solution.

PREPARATION OF A 83% SENSOR SALT SOLUTION

The following materials are weighed together and processed as before:
120 g. 10% potassium polyacrylate solution
338 g. distilled water
30 g. M/40 zinc acetate solution
12 g. 4% potassium borate
100 g. 2M potassium 3-(4-ethylbenzoyl) propionate
1 g. Monsanto's HB40

Summarizing, acids can be readily synthesized from which humidity-responsive alkali metal salts can be easily prepared. Solutions of such pure salts can be readily coated onto a variety of substrates to produce primary, nondrifting humidity sensors of great accuracy. The readout can be either in optical or in electrical capacitance changes or in both. The humidity range which such salts can cover is large, and by incorporating readily prepared lattice modifier salts as well, the range is substantially expanded.

Compounding such pure, prime sensing salts and their lattice modifiers with appropriate polymers, heavy metal salts, borates, and lattice stabilizers creates compositions unusually well suited for industrial coating. Such coated substrates can be used in direct readout hygrometers, electronic hygrometric controls, electronic hygrometers hygrometric limit arms, and many other devices.

Turning again to the various hygrometric devices which were described earlier in a general way, the simple transmission-type sandwich of FIG. 3 represents an excellent answer to the need for a humidity alarm for the myriad rooms in which are stored goods of value which can be damaged by high relative humidities. The device can be readily hung near a window or a lamp and thus be suitably illuminated. A coating of a sensor composition of 0.01 mm. thickness or less results in a brilliant optical readout.

The reflection-type sandwich of FIG. 4 is a most convenient device to set into the wall of sealed, humidity-sensitive enclosures (such as electrical junctions and switching boxes where condensation of moisture introduces serious electrical and corrosion problems). In such an installation the humidity-sensor has free access to the enclosure air, the circular-type polarizer 20 can be readily installed hermetically in a small aperture in the outer wall of the box, and illuminating beam 5 is supplied by room light or by a flashlight.

The graded series of humidity sensors found in the device of FIG. 5 can range from 15% RH or lower to 85% RH or higher. Though the illustration shows 10% RH intervals and a 30% through 90% RH range, compositions having RH intervals of 5%, 2.5%, or any convenient interval can be used. The RH range can also be selected to suit the needs of the particular device, The sensors in the illustration are accompanied by RH legends since the degradation of stored goods is best gauged in terms of the RH to which the goods are exposed. However, the trigger points of the various plaques can be indicated in absolute humidity terms if desired. The sensors of the ore, sent invention trigger at aqueous vapor pressures ranging from about 0.1 to 17.5 mm. of mercury at 20° C.

FIG. 6 is a classically simple embodiment of a capacitance-type humidity sensor, As noted before, it offers great accuracy as well as a unique and simple mode of optically checking the electrical integrity of the capacitance-measuring circuitry by noting the capacitance readout at the point of optical phase shift.

Ordinary secondary, capacitance-type, polymeric humidity sensors function by sorbing water vapor. Their capacitance vs. RH curve is substantially non-linear. Thus, complex electrical networks are used in an attempt to correct each hygrometer's readout to a linear one. However, the shape of a polymer's capacitance vs. RH curve changes as the polymer ages. This complex shift cannot be compensated for. Indeed, although so-called "aqueous humidity calibration salts" are furnished with secondary capacitance-type hygrometers in order to aid in field correction for other types of drift, such field compensation is not successful.

In contrast, the primary humidity-sensing salts of the present invention are highly stable, definite chemical entities. They can be readily used in a pure, uncompounded form in high precision hygrometers of the capacitance-type, of the optical type, or of a combination type.

An as example, pure cesium benzoylpropionate, in the form of a thin film in a sensor 3, such as FIG. 6, generates a strictly linear capacitance vs. RH curve over the RH range of 22% through 72%. An explained before, linear extension of this range is readily accomplished. Further; this simple sensor has the same sensitivity, namely 0.1–0.2 pF/1% RH/sq. min. of film, as the finest secondary, capacitance-type sensors which have been developed over the years. In short, the new technology offers at low cost a number of unusual features of great importance in the humidity-sensing field.

There are a few important applications for humidity sensors where exceptionally rigorous conditions are encountered during their life cycles. Perhaps the best known example of such unusual circumstances is the 500° C. cycle to which humidity sensor chips are exposed during the hermetic sealing of military-type ceramic "packages" which house integrated circuits. The sensor chips (which have been secondary type sensors until now) are sealed within the package to monitor its interior humidity, the electrical connections being brought out through package pins.

Secondary type capacitive or conductive sensors offer many problems since the sensor within the hermetically sealed package cannot be standardized after firing. Thus, there is a real need for primary type, non-drifting sensors such as those of the present invention. Unfortunately, though the organic type sensors of this invention are exceptionally stable, they cannot withstand 500° C. firing. such applications I have found inorganic hydrates of great utility. Typical of the chemical compounds which may be used in capacitance-type, humidity-responsive devices which may be cycled to elevated temperatures are these: calcium chloride, barium perchlorate, magnesium perchlorate, calcium sulfate, calcium bromide, and copper sulfate.

Calcium chloride typifies a salt I have found most useful as a capacitance-type sensor since it may be cycled to 500° C. for an extended period and still retain its primary humidity sensing characteristics.

I have found that the finely inorganic compounds which are so useful in compounding the organic sensor salts of the present invention (and which I have discussed before) also are very effective in the compounding of these inorganic salts as as to secure high sensitivity and freedom from deliquescence problems. It is theorized that the sensor coatings of these very high surface area materials are only a few molecules thick and so are very responsive. As an example, a 0.25 molar solution of chemically pure calcium chloride, thickened with frown about 0.5 to 4.0 percent by weight of a pyrogenic silica (200 sq. meters surface area/g.) forms a most effective coating suspension. The curve of capacitance vs. RH of such a sensing film gradually slopes upward from about 5% RH to 15% RH at which point there is a large and almost vertical rise before resuming a linear slope. It is an excellent curve with which to track the critical 8 to 20% RH range within the "sealed" package so as to easily detect micro leaks.

I have found that calcium bromide generates a capacitance vs. RH curve which is of the same characteristic shape as that of calcium chloride, FIG. 8c, when compounded with the same silica. However, the large and almost vertical rise occurs at about 5% RH at 20° C. instead of the 15% RH characteristic of calcium chloride. Further, I have found that calcium chloride and bromide may be blended so as to secure capacitance vs. RH curves in which the large rise occurs at intermediate humidities.

In summary, and as has been previously discussed, to create a graded series of humidity sensors where optical trigger points vary from 15% RH to 85%, m typically select a sensor salt from the potassium and/or cesium alkali metal salts of benzoylpropionic acid and/or ethylbenzoylpropionic acid, stabilize it with an alkali metal perfluoralkyl acid phosphate, complex it with the alkali metal salt of a polymer with repetitive carboxyl groups whose acidic hydrogens have been replaced by the alkali metal cations (and which has been complexed with a selected polyvalent cation of a water soluble salt such as copper acetate along with an alkali metal borate), and, if desired, reduce its trigger humidity by adding a crystal modifier such as cesium hydroxybutyrate.

In another aspect of the invention, soluble complexes of the keto salts are provided.

BACKGROUND OF THE INVENTION

In my U.S. Pat. No. 4,975,249 I claim a humidity-responsive device wherein the primary humidity-responsive composition used comprises one or more alkali metal salts of a keto acid of the general formula R—Aryl—CO—X—$(CH_2)_Y$—$CO_2H$, where R is hydrogen, halogen, alkyl, alkoxy, or nitro, where Aryl is phenyl, or a connected ring structure or a fused ring structure, where X is nitrogen or a carbon attached to the adjacent carbon with either a single or a double bond, and where Y is 0 to 7.

The primary-type sensor compositions operate by chemically reacting with the water vapor of the air at precise, reproducible humidities, shifting from a hydrated, birefringent phase to a deliquesced (dissolved), non-birefringent phase. Such phase shift points, and thus the humidity responses, are a function of the alkali metal cations and the keto acid anions used. They may be further modified through the addition of what I term "lattice modifiers," which are alkali metal salts of a certain general structure.

Further, in order to modify the physical and chemical properties of these salts and so make them more useful as humidity sensors, the alkali metal salts of the primary acids specified and of the lattice modifier acids specified may be usefully complexed with polymers. These contain repetitive oxygen-bearing groups including the hydroxyl, the carboxyl, and the sulfonic acid groups or mixtures of them repetitively present along a substantially linear chain. Examples of these polymers are as follows: polyether group—polyethylene oxide; polyamide group polyvinylpyrrolidone; carboxyl group—poly(methylvinylether/maleic anhydride), poly(styrene/maleic anhydride), polyacrylic acid; sulfonic acid group—polyvinyl sulfonic acid; methoxy group—methoxy cellulose. In the U.S. Pat. No. 4,975,249 a polymer which has repetitive carboxyl groups whose acidic hydrogens have been replaced by alkali metal cations is claimed.

In my pending divisional patent application (Ser. Nos. 07/562,017, filed Aug. 2, 1990, of continuation patent application Serial No. 07/444,559, filed Dec. 1, 1989, which is a continuation patent application of Ser. No. 07/078,186, filed Jul. 27, 1987) I claim chemical compositions comprising one or more alkali metal salts of the acids of the general formula given above, the salts being Complexed with one or more polymers containing repetitive oxygen-bearing groups along a substantially linear chain. In another claim of said application I specify that the polymers be selected from a member of the group consisting of polyether, polyamide, polyhydroxy, polycarboxy, and polysulfonic acid polymers.

The phase shifts of both the uncomplexed salts and of the polymer complexed salts are accompanied by both optical and electrical changes, the electrical changes including changes in both capacitance and conductivity. Such changes, and especially the optical and capacitance changes, generate signals which can be readily used for the indication and control of humidity.

The alkali metal salts of the acids of my general formula are remarkable because they are progenitors of "lyotropic liquid crystals." They are amphiphiles, compounds possessing an organic ring structure that is water insoluble (hydrophobic) and a side chain with a polar head (ionic) which readily dissolves in water (hydrophilic). Though I do not wish to be bound by theory, I hypothesize that under suitable conditions the cation of the side chain bonds to the oxygen of the benzoyl group of a typical salt to form a novel polar ring which is highly susceptible to solvation because of its ionic nature. This compact, multi-ring structure which forms is believed to be unusually suitable for the formation of lyotropic liquid crystals.

The "liquid crystal state," of course, is that unusual intermediate state in which the molecules are not as organized as they are in the solid state where constituent molecules execute small vibrations about firmly fixed lattice positions but cannot rotate. Nor are the molecules characterized by relatively unhindered rotation with no long-range order as they are in the liquid state. Rather, in the liquid crystal state the molecules have a good deal of molecular order, intermediate between solid and liquid.

My lyotropic liquid crystals result from the reaction of a ligand-type "solvent" with the cation of the keto salt. "Ligand," as used here, refers to any chemical species capable of binding strongly to metal ions, particularly alkali metal ions. To remove any ambiguity, the term "solvent" as used in this patent application is simply an acceptance of the fact that many of the ligands I use are referred to as solvents in the literature because their ligand properties often are not pertinent. They are used, for example, as solvents for or plasticizers of a wide variety of polymers. In contrast, I use these chemical compounds as ligands for the alkali metal cations of my keto salts and not as solvents.

Water is the ligand, of course, in the case of my liquid crystal progenitor salts when they are being used for humidity sensing. As is true of lyotropic liquid crystal salts in general an excess of the ligand "solvent" (water vapor in humidity sensing) converts their lyotropic phase into a true solution. In optical sensing, of course, the invariant transition from the liquid crystal phase to the non-birefringent, solution phase (at a particular humidity level) is accompanied by a substantial optical signal shift, which may be further amplified if desired.

My patent cited and my pending divisional application makes clear that the affinity for water of the alkali metal salts of acids of my general formula can be greatly modified by selecting a suitable structure. For example, alkylation of the phenyl ring of benzoylpropionic acid greatly reduces the affinity of its alkali metal salts for water vapor. Thus, they deliquesce at much higher humidities than the non-alkylated salts. This greatly reduces the water affinity of their polymer complexes as well.

As one would expect, there fare various uses for these versatile salts and their polymer complexes other than as humidity sensors since the alkali metal salts are electrolytes and their polymer complexes are what are often termed "polymer electrolytes" or "polyelectrolytes." If the materials, especially the polyelectrolytes, are to be used in the "ordinary world," the world of ubiquitous water vapor, the simple control over water affinity described above is a very useful property if, for example, an antistatic polymer composition is desired. However, there are other uses for electrolytes, for example in sealed alkali metal batteries, in electrochromic windows, and as initiators in anionic polymerization where water is highly deleterious and where an effectively functioning anhydrous system is essential.

If thin layers of aqueous solutions of my salts or their polymeric complexes are deposited on suitable substrates and dried by heating, especially in a vacuum, much of the water ligand can be readily removed. However, it is well known that the last small quantities of water coordinated with alkali metal ions in the crystal lattice of any salt are removed with great difficulty because of the stabilizing nature of the lattice. Ligands which are water analogs, such as glycols, glymes, etc., can be added to the water solutions of the polyelectrolytes, for example, before drying to replace the water ligand and so ease the task of water removal. But the procedure remains slow and expensive, ill suited to a large volume industrial operation.

One possibility might seem to be the use of an anhydrous water analog such as methanol as a ligand-type solvent for dissolving and reacting thoroughly dried, finely powdered alkali metal salts (of the acids of my general formula) with polyethylene oxide (PEO) to prepare polyelectrolytes. It works well. However, it is almost as difficult to remove the last traces of methanol from the polyelectrolyte so formed as it is to remove water. Like water, methanol is a protic solvent, one which is not inert to lithium and sodium metal. Thus, it is completely unsuited for preparing alkali metal battery electrolytes.

What is needed for many purposes are non-aqueous, ligand-type solvents for my alkali metal keto salts. Then, after the salts are thoroughly, inexpensively dried as finely divided particles, they can be solubilized as concentrates. These liquid complexes, if desired, can then be further dried (and concentrated, concurrently) in a wiped film, heated, vacuum still before compounding. Further, such ligand-type solvents should include "aprotic" types for dissolving salts for use in reactive systems.

Aprotic solvents are often defined as ones which are "inert," an ambiguous term. Although they contain hydrogen atoms, they cannot donate suitably labile hydrogen atoms to form strong hydrogen bonds. However, as I have noted, some of my salts complexes are used with polymers as electrolytes for sodium and lithium metal batteries. Therefore, aprotic, ligand-type solvents of exceptional stability also are required. In general then, great care must be used in choosing among protic, ordinary aprotic, and aprotic ligands of superior stability so as to match the requirements of a particular system.

There is another requirement of importance, namely, the ability to make solutions of these complexes which are concentrated. Thus, the polymer/salt content of the polyelectrolyte (which results from compounding the required amount of the salt complex with an appropriate polymer to form a polymer complex) will be high enough to give solid films of good physical properties for use in battery assemblies, electrochromic windows, etc.

Water, as a ligand-type solvent, is superb, in part because its powerful hydrogen-bonding properties gives it great reactivity and thus solvency. The non-aqueous, protic, ligand-type solvents, though poorer than water, are still much better than aprotic solvents in creating complexes of high salt concentration. The worst are the aprotic, ligand-type solvents and this is especially true with respect to my salts. There is a reason for this.

Standard alkali metal salts used in formulating polyelectrolytes have their cations freely exposed to available ligands. As a result, they readily complex with polymers such as PEO in a variety of solvents or even when simply thermally milled or processed with the polymer at a suitably elevated temperature.

In contrast, the cation of one of my anhydrous, alkali metal salts is believed to be locked into a ring structure, as I hypothesized earlier. This structure gives the salts many remarkable and useful properties as my patent describes. However, as a corollary effect is a lattice structure so stable that the salts are insoluble in a wide variety of ordinary excellent aprotic, ligand-type solvents, even when heated for an extended period. In short, molar cohesion and steric factors appear to prevent ligands front reacting with and solubilizing the cation locked in the ring. Thus, the problem of preparing complexes based on my salts and aprotic ligands is most challenging.

SUMMARY OF THE INVENTION

The present invention provides novel chemical compositions in which the alkali metal salts of acids of my general formula, $R-Aryl-CO-X-(CH_2)_y-CO_2H$, are complexed with ligand-type "solvents," especially aprotic types, in such a way as to give soluble complexes. It is often convenient to form a solution of the complex by using an excess of the same ligand-type solvent as that which is used to open the crystal lattice and form the usually solid complex. For when a solution is prepared it is easier to be certain that all of the anhydrous, alkali metal salt particles have been reacted to form the complex.

Nevertheless, it is the primary complex itself which is my primary focus, whether or not a solvent for the complex is present and whether or not the solvent used is the same as the primary ligand or different from it. Further, it should be emphasized, that though I may use an excess of the aprotic, ligand-type solvent for ease of laboratory preparation, I choose to use the minimum excess possible. This then allows the maximum latitude possible in the formulation of a liquid, paste, or solid electrolyte using the salt complex.

Though the acids of my general formula permit the preparation of many alkali metal salts, the lithium salts of hippuric acid, methylhippuric acid, benzoylpropionic acid, and methylbenzoylpropionic acid typify salts which are especially useful in the preparation of complexes for use in the preparation of complexes for use in preparing various electrolytes and polyelectrolytes. As I have noted before, these salts are essentially insoluble in a broad variety of good aprotic solvents. Typical liquids include propylene carbonate, dimethylformamide, cyclohexylpyrrolidone, ethylene carbonate, dimethylacetamide, diglyme, triglyme, tetraglyme, gamma-butyrolactone, and many others.

As a result of extensive research I have discovered novel combinations of ligand-type chemical compounds which function in new and unexpected ways to allow the rapid and complete opening of the crystal lattices of the alkali metal salts of the acids of my general formula in which a nitrogen has replaced a carbon in the oxygenated chain/ring. These are typified by the hippurates where the individual salt molecules are very tightly bound in the lattice. With the opening of the lattice, the individual molecules are released as soluble complexes so that they are available for various further complexing reactions (with polymers, for example).

I also have discovered still different combinations of chemical compounds which function in new and unexpected ways to allow the rapid and complete opening of the crystal lattices of the alkali metal salts of the acids of my general ,formula in which there is no nitrogen in the oxygenated chain/ring. This group is typified by the benzoylpropionates, and their lattices are still more difficult to open than those of the hippurate type.

I have further discovered chemical compounds which are useful auxilliary ligand-type solvents in opening the lattices of these salts so that they may be effectively used.

DETAILED DESCRIPTION OF THE INVENTION

I have noted that a remarkable property of these salts is their insolubility in a wide variety of aprotic, usually effective ligand-type solvents. Ordinarily, a salt dissolves in a ligand-type solvent to form a solution if either the ion-pair solvation energy or the total of anion solvation energy, cation/ligand reaction energy, and the "dissociating or ionizing power" of the solvent exceeds the lattice energy of the salt.

This is especially true if sufficient ligand molecules are furnished to provide not only the necessary number of ligands to properly coordinate each cation in its "inner sphere" complex but also to provide ligands for its "outer sphere" environment. In aprotic ligands these salts simply do not respond as most salts do even when sufficient ligands for both spheres are present.

Though I do not wish to be bound by theory, I hypothesize that with these alkali metal salts solvation is very limited because of steric factors and because the molar cohesion of certain groups in the oxygenated ring especially is very great. For example, the molar cohesion (in cal./mole) of the NCO group of the hippurates is 16,200 whereas that of the $CH_3$ group is only 1780. Thus, the cation's opportunity for ligand reaction and dissociation is very limited since it is bound in a ring which, in turn, is strongly bound to other rings in the crystal lattice. The net effect is insolubility, even in heated, ligand-type solvents.

Unexpectedly, I have found that a remarkable transformation occurs when a suitable polymer is added to such an insoluble salt dispersed in an appropriate heated, aprotic, ligand-type solvent. Reaction of the triad of polymer, salt, and ligand-type solvent takes place and the salt and polymer promptly dissolve to give a clear solution. For example, polyethylene oxide (PEO) can be added to a slurry of lithium hippurate in dimethylacetamide (DMAC) at 110° C. to quickly produce a clear solution.

Though I do not wish to be bound by theory, I hypothesize that appropriate ligand-type solvent molecules containing the NCO group, with its high molar cohesion, complex to a very slight degree with the salt cations and, concurrently, reduce the intermolecular attractive power of the adjacent NCO groups of the hippurate molecules. Thus, a few molecules of complexed salt are released from the binding forces of the salt lattice. Each molecule released from its crystal lattice is immediately captured by the ether oxygen of the PEO. Thus, the solution equilibrium shifts to the right and the salt quickly dissolves. In the absence of the sequestering ether oxygen the equilibrium is not shifted and so solution does not occur.

Having established that a suitable triad can bring opening of the salt lattices and complexation, it is essential that the components are compounded properly. This means forming useful solid or liquid polyelectrolytes in which all of the components are present in such ratios as to produce stable systems of good conductivity and satisfactory physical properties. If liquid or paste complexes are desired, it is satisfactory to compound in such a way that the (polymer:salt) molar ratio is at least 4:1 and sufficient ligand-type solvent is added with heating and mixing to complex and solubilize the components so as to produce the desired product. Or, as I have discovered and will subsequently discuss, the 4:1 (polymer:salt) molar ratio can be substantially reduced so long as the ligand-type solvent content is raised so that the ([polymer plus the ligand-type solvent]:salt) molar ratio is maintained at from 4:1 to 16:1.

I term this a "minimum polymer/maximum salt" system. Such pastes or liquids as result can be used in those forms or they can be used in what can be termed a "two-stage" process to produce a solid complex. The second stage of the two stages of such a process consists of thermally fluxing such a paste or liquid into additional PEO, for example, in a Banbury mixer or its equivalent.

In a "single stage" process a solid complex can be produced directly by using the same components but in different ratios. The treatment is similar to the second stage processing just described. The three components are fluxed in a heated mixer such as a Banbury or on a two roll mill. But only a minimum amount, empirically established, of a ligand-type solvent is fluxed with a polymeric type of ligand such as PEO furnishes, along with the salt. Since these complexes are labile (especially at elevated temperatures), rapid dissociation and association occurring, the amount of solvent ordinarily can be reduced to a much lower concentration in a heated, high shear operation than in the two stage process.

Just as polyethylene must be heated to a temperature where much of its crystallite content melts before it dissolves into a solvent, the heating and fluxing of a polymer such as PEO with the complexing salt and a ligand-type solvent at as high a temperature as is consistent with the polymer's stability assists in opening the lattices of both the polymer and the salt and so creates an optimum, homogeneous complex. Antioxidants may be included in these systems, of course, to secure good stability at the elevated fluxing temperature at which rapid, complete reaction best occurs.

The dynamic nature of these systems often allows a further useful variation of these processes. That is, substantial amounts of the "NCO" type of ligand can often be replaced by less active, complementary types of ligands such as ethylene or propylene carbonate furnish.

Turning back to the "minimum polymer/maximum salt" process mentioned earlier, I have discovered that in this process the polymer can be reduced far below that required to meet the 4:1 (ether oxygen: cation) ratio established in many polyelectrolyte studies reported in the literature. Indeed, I have found that rapid solubilization of the salt in an amide ligand occurs when so little PEO is added that instead of each lithium cation being coordinated and stabilized by four ether oxygens each cation is solubilized by as little as one third of an ether oxygen. That is, every ether oxygen from the PEO polymer solubillzes three lithium cations, yet solution of the salt still occurs rapidly. Unexpectedly, these systems are so dynamic that the polymer so essential for solubilizing can function at almost catalytic concentrations.

It is hypothesized that the amide ligands, for example, complex the cations of the salt molecules as they are dissolved. Concurrently the oxygen of the polymer's ether groups and the other available amide molecules continue to attack the undissolved salt crystal lattices until solution is complete. Once the salt is all dissolved, the (PEO:salt: amide) complex can then be thermally milled with more PEO to bring the (ether oxygen:cation) ratio of the complex to the 4:1 ratio which usually gives optimum electrical conductivity. Thus, for each PEO molecule used in preparing the salt concentrate additional PEO molecules can then be reacted with the concentrate to shift the (polymer ether oxygen: salt) molar ratio from 1:3 to 4:1 or higher.

Using this minimum polymer/maximum salt solubilization method to prepare a high salt concentration solution (for reacting with additional polymer) typically allows a reduction in the amide ligand concentration in the final electrolyte if the two stage process is used. Thus, a greater control of physical properties through appropriate compounding with other materials is possible. Nevertheless, in spite of this improvement which the minimum polymer/maximum salt process offers, the single stage process usually allows still greater reductions in the amount of ligand-type solvent needed.

I have discovered a valuable variation of the minimum polymer/ maximum salt process. I have found that polymers which I claim in my U.S. Pat. No. 4,975,249 and in its continuation patent application (and which are not the primary focus of contemporary polymer electrolyte developments as PEO polymers are) can be used to prepare still more concentrated salt solutions. Such a change is of importance since there is a limit to the number of cations which a single molecule of PEO ether oxygen can solubilize. For example, when more than about three cations (per ether oxygen from PEO) are introduced into a dimethylacetamide:hippurate mixture an opalescent "solution" is secured rather than a clear one. I hypothesize that this reflects the net effect of the complex equilibria which exist in these dynamic systems.

As an example of my superior systems, I have found that each molecule of the polyamide polyvinylpyrrolidone(PVP) compounded with the same salt and aprotic, ligand-type solvent as was used with PEO, solubilizes seven cations while producing a sparkling clear solution, even at reduced temperatures. Thus, much larger quantities of PEO can then subsequently be fluxed into such a (PVP:salt:amide) concentrate to raise the (oxygen:cation) molar ratio to 4:1 or higher in the final stage of the two stage process. Such a complex, of course, contains a little PVP. But this polymer is known to be an effective component of polyelectrolytes, its disadvantage having been its high glass transition temperature when used alone.

I do not wish to limit the use of these potent polymer adjuncts to two stage processing. Thus, front a minimum of about 0.5 mole percent of polyvinylpyrrolidone (on the weight of PEO) to a substantial, empirically established maximum can be included in a single stage thermal fluxing of (PEO:salt:ligand-type solvent) to improve processing as well as the product.

In summary, for adequate salt solubilization the salt cation must be complexed with some suitable type and number of ligands. These, of course, can be mixed ligands so long as one is an NCO type or its equivalent. As I have explained, the ligands I use are partly non-polymeric and partly polymeric, the molecular ratio between the two being selected to create an effective triad. As noted before, four ligands to coordinate the "inner sphere" of each alkali metal cation are generally accepted as the minimum needed. Several times that amount assist in stabilizing the "outer sphere" of each cat icon.

During the two stage process of preparing a solid complex the polymeric/non-polymeric ligand ratio usually shifts substantially. For example, starting with the minimum polymer/maximum salt system, the salt's ligands are largely of the non-polymeric type, but in the final electrolyte are largely of the polymeric type due to the additional. polymer fluxed in. In contrast, the single stage fluxing process is essentially a constant ratio process, the optimum ratio being empirically established.

Having considered typical salts and polymers useful in formulating these triads, it is appropriate to consider the aprotic, ligand-type solvents which can be used effectively. Earlier I noted that the NCO group of the oxygenated ring of the hippurates has an exceptionally high molar cohesion or intermolecular attractive force. Thus, I hypothesize that it is these forces which are so effective in bonding such salt molecules together. I further hypothesize that somewhat comparable forces are required of ligand-type solvents to join with appropriate polymers to solubilize the salt by interacting with the salt to open the lattices.

I now have found that many compounds bearing the same NCO group present in the hippurate salts are indeed potent ligand members of (polymer:salt:ligand) triads. Further, it is interesting to note that the same NCO group is found in the polyvinylpyrrolidone which has proved so effective as the polymer member of a triad which included dimethylacetamide as the solvent-ligand member.

Though such protic amides as dimethyl formamide (DMF) is excellent as a ligand solubilizer, I prefer to use these amides which are not only aprotic but inert to sodium and lithium as well. It is true that under certain circumstances passivating films may form on reactive metal surfaces in electrochemical devices such as batteries. Thus, ordinary aprotic or even protic ligands, as members of triads, might not attack electrodes, for example. Nevertheless, aprotic ligands, and especially the very stable ones, are often the safest type to use for a variety of polyelectrolytes. In summary, a formulator must weigh the final application carefully in selecting the ligand to be used.

Among the suitable aprotic, ligand-type compounds having excellent stability in the presence of sodium and lithium metals are the following amides: N,N-dimethylacetamide, N,N-dipropylacetamide, N,N-dimethylbenzamide and hexamethylphosphoramide. However, dimethylformamide, 1-acetylpiperidine, pyridine-N-oxide, N-methyl-2-pyrrolidone, 1-acetyl-4-piperadone, N,N-diethylacetamide, N,N-dimethylpropionamide and 1-cyclohexyl-2-pyrrolidone typify other amides which are useful under conditions which are not so demanding.

The ureas, of course, can function as ligands since they have NCO structures analogous to the amides. Tetraethylurea (TEU) appears to be quite inert in contact with lithium and sodium. Other alkylated ureas, urea, the polyureas, and the the thioureas are applicable as ligands where conditions are appropriate.

The NCO isocyanate group is unusual in that in the diisocyanates it can be difunctional. It can be used as a ligand to complex and solubilize my keto salts. But with appropriate catalysts the same diisocyanates can be reacted with polyether diols (polyethylene oxides), dihydric and polyhydric glycols, and polymers terminating in hydroxyl groups to form polyurethanes and polyureas having superior physical properties.

Thus, there is an opportunity to use the diisocyanates both as ligands to open the lattices of my salts and so solubilize them and as reactants to build a polyetherurethaneurea network of superior physical properties whose ether groups are available for complexing with my solubilized salts to create superior complexes.

The formation of polyurethanes is inherently a process capable of wide variation because of the many basic components which are readily available. The number of polymers which can be readily prepared from 2,4 tolylene, 2,5 naphthalene diphenylmethane, and the many other diisocyanates available and the polyethylene oxides, polyethylene glycols, and glycols (all of which are available in a wide range of molecular weights) is very large. Further, my complexing salts, to be reacted with the polyether groups of the polymers formed, can be rendered soluble not only by isocyanate groups but by other aprotic, ligand-type solvents which may be included in the composition, such as appropriate amides which are often used in standard polyurea and polyurethane compositions as plasticizers of the polymers. Thus, various mixtures can be used to obtain superior results.

The polyfunctional isocyanate group is of special interest as a component of complexes prepared by what I have termed the "single stage" process since it offers an effective way of improving the physical properties of the solid complexes based on PEO. Many investigators working with polyelectrolytes based on standard PEO as the sole polymer complexed with sodium and lithium salts have noted the softness of the complexes formed and the problems which such poor physical properties cause in producing useful electrochemical devices. Thus, if the isocyanate groups which assist in solubilizing my salts can contribute to upgrading the physical characteristics of the complexes which result when the salts react with the polyether groups of the PEO-bearing, isocyanate-based polymer, it is a valuable feature.

One well known type of material is what is often termed a "prepolymer." It can be made, for example, by fluxing a polyether diol such as PEO with an excess of diisocyanate on a two-roll mill or in a Banbury mixer to create a prepolymer bearing reactive NCO end groups. If water is then added to the polyurethane which has been formed, the NCO end groups react with the water to form polyetherurethaneureas having superior physical properties.

Since glycols react with the isocyanate group just as water does, water, a ligand which complexes my salts so well, can be supplemented by appropriate glycols (which also are effective ligands for my salts). Thus, one can prepare a (salt:water/glycol ligand) complex in which the salt's lattice has been opened and each salt molecule complexed with water/glycol. The water can then be stripped from the complex to a low level to develop a complexed (salt:glycol) solution to be reacted with the prepolymer to form a polyetherurethaneurea while simultaneously complexing my salts with the ether groups of the polymer.

In actual practice, it is difficult to insure complete reaction of residual water in the complex with the isocyanate groups so that absolutely no traces of water remain to react if such polyelectrolytes are used with lithium or sodium electrodes. Thus, such polyelectrolytes are more suitable for less demanding applications than electrolytes in alkali metal batteries.

In a sealed Banbury mixer it is possible to exercise close control of the temperature, the degree of shear, the time of mixing, the rate of addition of reactants, the atmosphere over the batch, etc. Thus, single stage processing in Such equipment offers many advantages and opportunities.

A suitable diisocyanate can be selected as the ligand-type solvent for the salt and the diisocyanate can be supplemented as necessary with a suitable ligand such as an amide. The (diisocyanate:salt) solution can then be reacted with a polyether diol. The resulting product can then be further reacted with a diamine to form a polyetherurethaneurea, if desired. Concurrently, the salt is available for complexing with the ether groups. Finally, the polymer end groups may be capped with a suitable chain terminator such as ROH or $RNH_2$.

A variant of this is to complex the anhydrous salt with a protic, ligand-type material such as 2-methylpentamethylene diamine. This complex is then slowly fluxed into a diisocyanate/PEO prepolymer to form a polyetherurethaneurea. Concurrently, the salt is made available to complex with the ether groups. Again, the polymer end groups may be capped.

Another approach is to flux the anhydrous salt directly into the prepolymer, which may contain an amide to assist in opening the salt lattice as in the single stage process described before. A diamine may then be added to form a polyetherurethaneurea of good physical properties and the polymer end groups may then be capped as before.

Still another mode of introducing the salt into the prepolymer so as to complex with its ether groups is to use s concentrate prepared using the minimum polymer/maximum salt process described before. An amide such as dimethylacetamide can be used as the ligand since it is often used in standard prepolymers to improve reaction rates. A diamine can then be used to form the polyetherurethaneurea which can be end capped.

To prepare the optimum polyelectrolyte complexes it is desirable to prepare polymers having superior physical properties such as toughness and flexibility which have the maximum number of polyether groups available for complexing with my salts. This generally means using polyetherdiols such as PEO having molecular weights of a million or more and a diisocyanate concentration of approximately 5–20% of the PEO prepolymer present.

In closing this very brief discussion of the preparation of polyurethanes, polyureas, copolyureas, and the myriad other excellent polymers which can be made using the many raw materials available, and which are capable of complexing with and solubilizing my salts because of the NCO groups common to the ureas, isocyanates, urethanes, and amides, I wish to emphasize that I do not wish to limit myself to the few structures and methods I have mentioned as examples. For preparing these polymers so as to enhance certain properties is as much art as it is science at present. Therefore, those skilled in compounding standard polyureas and polyurethane polymers will be able to use my salts with myriad compositions of this type using my basic approaches to the problem of solubilization.

Now, having commented at length on the various modes of using nitrogen-bearing keto salts such as the hippurates and the alkylhippurates, it is desirable to comment on the use of the other major salt group, the non-nitrogen-bearing salts derived from the acids of my general formula. In my section, "Summary of the Invention" I noted that the lithium salts of both the hippurates and the benzoylpropionates typify snits which are especially useful in the preparation of complexes. I have chosen to first focus on complexing the hippurates because they readily complex and dissolve if the appropriate members of the triads I have discussed are selected.

Unexpectedly, when aprotic, ligand-type solvents bearing NCO groups (such as I have described in detail before) are combined with a suitable polymer and an alkali metal benzoylpropionate (or its alkylated version), there is often little or no complexing of the salt. That is, these salts do not respond as the hippurates do. Nevertheless, it is highly desirable that complexes with no nitrogen in the oxygenated ring be readily available for preparing complexes since the ring strain, the steric aspects of the oxygenated ring with respect to the phenyl ring, the free volume of the final copolymer complex and similar factors are different from what is secured with salts from acids with nitrogen in the ring. These are all factors which affect polyelectrolyte performance.

As a result of extensive research I have found that solubilization of the alkali metal benzoylpropionate type of salts readily occurs if a modified triad is used. To modify the triad, at least a small percentage of the amount of the alkali metal benzoylpropionate (or its equivalent) needed in the formulation is replaced by an alkali metal hippurate (or its equivalent from the nitrogen-bearing group of salts).

Though I do not wish to be bound by theory, I hypothesize that the hippurate first is attacked and complexed and thus solubilized as I have stated before. Then the hippurate complex in the presence of a suitable polymer, as before, has the ability to attack the benzoylpropionate lattice and open it to complexing and solubilization. From about 0.5 to 20.0 mole percent of the hippurate (or its equivalent) combined with from 99.5 to 80.0 mole percent of the benzoylpropionate (or its equivalent) work effectively.

Among the applications for my salts is that of using them to initiate anionic polymerization in a cyclic monomer such as ethylene oxide. Polyether polymers such as would result from Such a polymerization have utility as branches to attach to a suitable chloromethylated backbone polymer to create a superior branched polymer. Such initiators usually need activation with a suitable complexing agent to promote activation of the ion pair and dissociation of the cation of the salt. Such activation is sometimes performed with polyethers, crown ethers, cryptands, or certain tertiary polyamines.

My keto salts are readily dissolved and complexed by such primary amines as diethylenetriamine, ethylene diamine, and 2-methylpentamethylenediamine. In contrast, a tertiary polyamine often used in activating inorganic lithium salts—tetramethylethylenediamine (TMED)—does not dissolve the hippurates or the benzoylpropionates. However, I have now described various ways of dissolving my salts and I have found that I can readily add TMED to such solubilized complexes and still maintain solubility and stability. Thus, complexes of my salts and polyamines such as TMED can be secured through an equilibrium reaction of my solubilized salts with a particular ligand of unusual power to serve as an activator of a particular reaction. In such instances, polyethers, crown ethers, and cryptands may be used as complementary ligands to those already described.

Besides these modes of opening the lattices of my salts and complexing them with aprotic ligands of such excellence that clear solutions can be formed, there are others of lower solubility but which, however, can be of use in particular applications. Dimethylsulfoxide, sulfolane, benzenesulfonamide, p-tolueneethyl sulfonamide, and o-toluenedimethyl sulfonamide are representatives of this group.

In my U.S. Pat. No. 4,975,249 I claim a group of alkali metal salts as "lattice modifiers" of the alkali metal salts prepared from acids of my general formula. The acids from which these lattice modifier salts are prepared have the general formula R—CZ—(CH$_2$)$_Y$—CO$_2$H, where R is amino, hydroxyl, carboxyl, or methyl, where Z is hydrogen, hydroxyl, or a keto, and where Y is 0 to 4. I have found that complexes of these modifier salts can be prepared just as I have prepared the complexes of the primary alkali metal salts of the acids of my general formula. Such complexes of the modifier salts can be used alone or in conjunction with the complexes of the primary alkali metal salts.

EXAMPLE 1

5 g thoroughly dried polyethylene oxide (Union Carbide WSR N-10) was dry mixed with 5.25 g thoroughly dried, powdered, lithium hippurate. 39.5 g dry dimethylacetamide was added and the slurry stirred while being heated at 110° C. The birefringent particles of the hippurate salt rapidly reacted with the polymer and the amide and dissolved to form a non-birefringent, translucent, soft paste at room temperature.

The molar ratios in this complex were 4:1:16 (polyethylene oxide: salt:amide). Heating with an additional amount of amide resulted in the formation of a clear solution at room temperature. The molecular weight of WSR N-10 is about 100,000 and the number of ethylene oxide repeating units is about 2270.

EXAMPLE 2

0.47 g thoroughly dried polyvinylpyrrolidone (BASF K-90) was dry mixed with 5.25 g thoroughly dried, powdered lithium hippurate. 39.5 g dry dimethylacetamide was added and the slurry stirred while being heated at 110° C. The birefringent particles of the hippurate salt rapidly reacted with the polymer and the amide to form a non-birefringent solution, clear even at reduced temperatures. The molar ratios in this complex were 0.15:1:16 (polyvinylpyrrolidone:salt:amide). The approximate molecular weight of the K-90 is about 350,000 and the number of repeating units is about 3150.

EXAMPLE 3

5.2 g thoroughly dried polyethylene oxide (Union Carbide WSR N-10) was dry mixed with 0.8 g thoroughly dried, powdered, lithium methylhippurate and 5.2 g thoroughly dried, powdered, lithium ethylbenzoylpropionate. 39.5 g of dry dimethylacetamide was added and the slurry stirred while being heated at The birefringent particles of both the methylhippurate and the ethylbenzoylpropionate salts reacted with the polymer and the amide and dissolved to form a non-birefringent, translucent, soft paste at room temperature. The molar ratios in this complex were 4:0.14/0.86:16 (polyethylene oxide:methylhippurate salt/ethylbenzoylpropionate salt:amide).

EXAMPLE 4

3.3 g thoroughly dried, powdered, lithium hippurate was stirred into 35 g of a polyurethane prepolymer (W. R. Grace Hypol FHP 4100) at 50° C. Almost immediately the hippurate salt particles dissolved and a brilliantly birefringent, liquid crystal type of solution formed. I hypothesize that the free NCO ligands terminating the prepolymer chains complexed with the salt molecules, opened the crystal lattice, and released complexed salt molecules for sequestering by the polymer's ether oxygens. As the salt complexes continued to react with the polyether groups of the chains the viscosity of the mass continued to rise until it set to a resilient solid.

The Hypol FHP 4100 is a viscous fluid containing 20% free NCO groups. It is prepared from methylenediphenyl diisocyanate (MDI) and polyethers containing a high percentage of ethylene oxide. From the data supplied by the manufacturer it is estimated that twelve polyether oxygen groups were present for each salt molecule I compounded into the material. As noted before, in a Banbury mixer operation much higher salt loadings are readily processed because of the power and high shear mixing available. Further, this particular prepolymer has not been optimized for this use but, rather, for making foams.

EXAMPLE 5

28.4 g of the salt complex solution of Example 2 (containing 3.3 g of dissolved lithium hippurate) was stirred into 35 g of the same polyurethane prepolymer (W.R. Grace Hypol FHP 4100) as was used in example 4. A clear, highly viscous fluid resulted. As complexing progressed the viscosity of the mass continued to rise until it set to a solid which showed no liquid crystal formation or crystallites. However, the clear solid did show some birefringence due to stresses frozen into the polymer matrix during solidification.

In another aspect of the invention, complexation products of lyotropic liquid crystals and inorganic compounds are provided.

It has been found that the novel chemical and physical characteristics of these alkali metal lyotropic liquid crystal salt complexes which make them uniquely suited as primary humidity sensors make them exceptionally well suited for a number of other critical applications. These include use in compounding superconductors, in preparing superior polymer electrolytes for alkali metal batteries, in formulating static dissipative plastics, and in preparing electrolytes for electrochromic windows. These novel characteristics have been noted in both the present specification and in the specification of my co-pending patent application U.S. Ser. No. 07/642,009 filed Jan. 16, 1991, entitled "Soluble Complexes of Keto Salts."

One key feature of these salt complexes is the tendency of the alkali metal terminated chain of a typical molecule such as sodium benzoylpropionate to loop around and close with the keto group to form a ring structure, thereby forming a two ring lyotropic liquid crystal structure analogous to that of a typical thermotropic liquid crystal. The intermolecular forces between such novel molecular structures cause them to assemble into liquid crystal "swarms" or arrays under appropriate conditions. Such arrays are characterized by extensive molecular alignment and organization.

To elaborate, my application Ser. No. 07/562,017 filed Aug. 2, 1990 is a divisional application which covers the compositions-of-matter which characterize these remarkable two ring complexes and the complexes which they form with suitable polymers. Because each of the rings can be readily modified greatly an immense amount of molecular design is easily and inexpensively possible so as to tailor the final salt complex to a particular need. In a general way, it can be noted that a typical lyotropic liquid crystal precursor salt complex is an alkali metal salt of an aryl substituted keto organic acid, the salt having an ionic polar ring complex phase. This has an organic aryl ring structure, and a ring formed from the keto group of the organic acid portion, intervening ring-members, and the alkali metal ion, the ring having at least 5 members in which the alkali metal ion is a ring member that bonds to the keto group to form the ring complex. The organic ring is hydrophobic and the polar ring which forms, and which may have from 5 to 13 members, is hydrophilic. One or more ring members are present between the keto and the carboxyl group, of course, when the complex ring is a 6 to 13 member ring. Since the organic ring may be varied widely and since the polar ring may be saturated or unsaturated, many permutations are possible.

Earlier I explained the advantages to be gained by compounding these complexes with finely divided inorganic compounds, noting that both the theological and electrical properties of systems can be so modified. The surface areas of such finely divided inorganic compounds can be as high as 50–200 meters/gram. Significantly, liquid crystal molecules are characterized by an unusual configuration which causes them to align to form liquid crystal "swarms." Such molecules also are known to sorb strongly onto surfaces. This powerful characteristic, of course, underlies the use of thermotropic liquid crystals in LC displays. My lyotropic liquid crystal salts also sorb strongly and, because these materials are alkali metal salts, adsorption, absorption and chemisorption are among the possible effects. The particular response depends on the general chemistry, the physical chemistry, and especially the surface chemistry of the selected inorganic materials. By selecting an appropriate inorganic compound or mixture of compounds to compound with these salt complexes and other components a great control over the physical and electrical characteristics of the complexation products which result is possible.

My keto salts of unusual structure are salts of the alkali metals. As noted earlier, the alkali metal of the carboxyl groups reacts with, or chelates with, the keto group to form a ring structure. It is well known that the complexes or chelates of the alkali metals are among the weakest known. This fact accounts for the low "stability constants" which characterize any of the alkali metal chelates formed by any particular "chelating agent." In sharp contrast, the stability constant of the copper chelate of any particular chelating agent is always very much higher.

Aluminum, whose finely divided oxide I recomended earlier as a compounding agent, has a stability constant even higher than that of copper. The stability constants of the chelates of calcium, barium, and strontium are intermediate between those of copper and most other metals. The net effect of this differential in stability constants is for alkali metal salt complexes to readily react metathetically with a wide variety of metal ions.

It is through metathesis that I am able to create exceptionally stable systems for use in humidity sensing by reacting my alkali metal salt complexes with both copper salts and with polymers containing repetitive oxygen-bearing groups along a substantially linear chain. In the same way, the metal ions available at the surfaces of finely divided inorganic compounds such as the oxides can form complexation products with my complexes.

Because of the unbalanced forces at such oxide surfaces it is easy for chemisorption to occur. Reaction is generally accelerated by heating, and so milling of heated, solid salt complexes and finely divided metallic oxides can bring formation of useful products. Solid salt complexes fluidized by complexing with liquid polymers such as lower molecular weight polyethylene glycols can also produce useful complexation products. If one is interested in superconductors, complexing under vacuum conditions followed by pressure consolidation to minimize micro-voids can be helpful in reducing micro-discontinuities and so enhancing conduction.

For superior results it is often better to Banbury the finely divided superconducting oxide particles under vacuum conditions with a heated, suitably fluid, truly anhydrous alkali metal salt complex. My "triad" method of solubilization described in my co-pending continuation-in-part application Ser. No. 07/642,009 filed in Jan. 16, 1991, entitled "Soluble Complexes of Keto Salts," provides such suitable fluid complexes. Degassing such complexation products is readily accomplished and excess ligand can be readily evaporated to a suitable level at the desired stage to bring about orientation of salt complex molecules.

In general, the "triad" method of solubilization is of particular interest in superconductor compositions, polymer electrolytes for alkali metal batteries, electrochromic systems, and other applications where anhydrous systems function best. Though the triad patent application's specification discusses modes of dissolving my salt complexes in water, alcohols, glycols, etc., its major focus is on water-free systems and especially those using aprotic, ligand-type solvents.

My anhydrous salt complexes are of very limited solubility in such solvents and especially in the anhydrous, aprotic solvents which are inert to such alkali metals as sodium metal. However, as noted before, my triad method readily produces concentrated solutions of my salt complexes suitable for use in a variety of applications.

Turning again to the finely divided inorganic compounds to be compounded with my complexes, they can be used in various useful ways. Alkali metal battery electrolytes containing my salt complexes can be liquids, pastes, or solids. In paste compositions finely divided inorganic compounds are useful in developing structure and establishing a yield value for the system which reduces the chances of leakage. For such purposes relatively inert inorganic compounds such as amorphous silicon dioxide can be of great value.

The same type of compound can be included with much more reactive metal oxides such as characterize many superconductors. Such blends allow rheological control over pastes designed for silk screen printing, for example. Again, relatively inert materials such as silicon dioxide or silicates can be usefully added to solid polymer electrolytes for batteries to give toughness and substantial yield value to the solid polymer film.

Because of the various effects which are sought through inclusion of finely divided inorganic compounds the appropriate concentration varies widely, ranging from a low 1% to as high as 98%. The lower concentration typifies the concentration needed to add a slight structure to a liquid system with amorphous silican dioxide. The higher concentration typifies a superconductor system where graded particle sizes are used so that the organic salt complex has few voids to fill. As noted earlier, the layer of salt complexes on the inorganic particles may be only a few molecules thick in some circumstances. In actual practice, the preferred concentration range of inorganic compounds is from 25% to 95% by weight.

A wide variety of superconducting, oxide-type powders are now available and can be compounded with my complexes to produce useful complexation products. Typical oxides are $YBa_2Cu_3O_x$, $YBa_2Cu_4O_x$, $BiSrCaCu_2O_x$, $Bi_2Sr_2CaCu_2O_x$, $Bi_2Sr_2Ca_2Cu_3O_x$, and $Tl_2CaBa_2Cu_2O_x$. Because of the high level of R&D being devoted to superconducting materials it is to be expected that new, superior compositions will become available in the future.

I do not choose to limit myself to the use of particular oxides such as I note above as components of my complexation products. Rather, I claim the use of my materials with inorganic compounds in general which are finely divided and which are superconductors. Generally, the preferred particle sizes fall in the 1–20 micron range, though larger sizes may be used.

In the oxide formulas noted above the number of oxygen molecules present has been indicated with an X. This is an acknowledgement that the field of superconductors is changing rapidly and is both art and science. As is well known, the oxygen content, with its great effect on the basic structure of the compound, has an enormous effect on the compound's superconductivity. In many cases the manufacturer of the superconducting oxide adjusts the oxygen level empirically, through process control, until the batch shows appropriate superconducting properties. Thus, in the case of a number of newer materials the oxygen level, as indicated by X, is not yet firmly established.

In the case of the well known material $YBa_2Cu_3O_x$, development has progressed to the point where one manufacturer is now able to offer a material in which X is held to $6.8 \pm 0.1$. Such progress can be expected to be made with the newer materials.

In the case of the Yttrium-type material the compound is related to the perovskites. These minerals contain 3 oxygen atoms for every 2 metal atoms. If the new material were an ideal perovskite, with 6 metal atoms in its unit cell, it would be expected to have 9 oxygens. In fact, it has between 6.5 and 7 oxygens. In other words, about one quarter of the oxygens are missing. The missing oxygens turn what would otherwise be a conventional, three-dimensional array into a unique layered structure which superconducts.

As noted above, my triad system of solubilizing my salt complexes produces liquids which are readily used in preparing superconductor materials, polymer electrolytes, etc.

Typically, a triad system consists of three key elements: one or more of my lyotropic liquid crystal precursor salt complexes complexed with one or more non-polymer ligands selected from members of the group comprising the amides, isocyanates, ureas, thioureas, and urethanes, with one or more polymeric ligands selected from members of the group of polymers containing repetitive oxygen-bearing groups along a substantially linear chain.

Among the non-polymeric ligands which are especially useful are dimethyl acetamide, dimethylbenzamide, dimethylformamide, tetraethylurea, N-methyl-2-pyrrolidone, and thiourea. My parent patent application identifies major classes of polymers which are suitable for complexing. Those classes include polyethers such as polyethylene oxide, polyethylene glycol, and alkoxy polyethylene glycol, polyamides such as polyvinylpyrrolidone, and polyhydroxy polymers such as polyvinyl alcohol.

My "triad" application describes a wide variety of ways to combine the many possible variants of each of the three basic elements of the system, namely, the precursor salt complex, the non-polymeric ligand, and the polymeric ligand. Thus, great control over the chemical and physical properties of the final products is readily secured. One especially interesting discovery is that exceptionally low concentrations of a suitable polymeric ligand can induce rapid solubilization of the ordinarily virtually insoluble salt complex in readily available NCO-type, ligand-type solvents such as dimethyl acetamide. NCO-type polymers, such as polyvinylpyrrolidone, make possible exceptionally stable, clear, concentrated solutions.

The triad system nicely illustrates that systems which use ligands which are different from water are basically the same as those where the ligand is $H_2O$. That is, they undergo the same type of phase shifts as hydrating systems do. Thus, a "non-aqueous, ligand-free lyotropic liquid crystal precursor salt complex" is the equivalent of an "anhydrous lyotropic liquid crystal precursor salt complex." On solvating the liquid crystal precursor with an appropriate amount of a suitable anhydrous ligand (either through controlling the vapor pressure of ligand over a film of the precursor salt or through compounding a known weight of the precursor salt with an appropriate weight of ligand) a shift to the liquid crystal phase occurs. This, of course, is analogous to the shift which occurs if the ligand had been water.

On reacting the liquid crystal phase with more anhydrous ligand (by applying the ligand vapor at a higher vapor pressure or by compounding a known weight of liquid crystal complex with additional ligand) the liquid crystal phase dissolves. This, too, is analogous to what happens with water systems.

These phase shifts can be reversed, of course, just as they can be with water systems. In the case of non-aqueous ligands the system's temperature must be adjusted to bring the vapor pressure of the ligand to an appropriate level to establish the phase desired. Thus, heating paste compositions laid down in film form and containing "excess" ligand can readily remove ligand to create the liquid crystal stage with its oriented molecules.

As noted before, for superconductor circuitry, pastes can be produced and printed onto suitable circuit boards and excess ligand solvent reduced to the desired level by evaporation so that a liquid crystal phase forms. For superconducting forms such as wires, plastic pastes can be produced, extruded, and the excess ligand solvent removed by heating. If desired, cross-linking agents and appropriate catalysts can be incorporated into the composition when the alkali metal salt complex is that of an unsaturated acid such as an aroylacrylate. Thus, cross-linking can occur during heating and/or exposure to suitable radiation so as to develop a tougher structure.

Instead of aroylacrylates being used, the alkali metal salts of "Pechman dyes" can also be used. These are the colored materials obtained when benzoylacrylic acid, for example, is heated with dehydrating agents.

In much the same way, by using inorganic compounds of high surface area which are not superconductors, and using cross-linking agents where desired, compositions with enhanced yield values, ranging from fluids to solids, can be prepared. These are suitable for use in polymer electrolytes for alkali metal batteries, for incorporation into plastics to render than static dissipative, etc.

One more aspect of my salt complexes of great importance in the formulation of these complexation products has to do with a discovery made during the development of humidity sensors, which also use these salts. The discovery was that appropriate alkylation of the aryl or equivalent groups of the salt complex could reduce the affinity for water to the place where the salts are essentially unresponsive to water vapor.

In the specification it is noted that potassium ethylbenzoylpropionate deliquesces at 83% RH though potassium benzoylpropionate deliquesces at 53% RH. In the same way, the hydration points of the anhydrous salts and their polymer complexes are raised through alkylation. Such inertness to water vapor is of great utility in manufacturing polymer electrolytes for batteries, superconducting materials, etc. which are unresponsive to the water vapor levels reached during the operation of such devices.

In another aspect of the invention, the reaction products of the lyotropic liquid crystal salt complexes are provided. This present application is the result of a continuum of R&D focused on the steady improvement of the materials disclosed. The latest, aroyl salt complexes, have shown themselves to have many applications and to be susceptible to to many structural improvements disclosed.

The R&D which led to the present materials began in the 1960's with an investigating program focused on the potential of special lyotropic liquid crystal salts. The investigation culminated with the discovery of the potential of the alkali metal salts of 3,3',4,4' benzophenone tetracarboxylic acid as inherently high precision, optical type, primary class, non-drifting humidity sensors. They appeared to have the properties with which to meet a world wide need.

By the early 1970's a full time program was developed and launched. This was directed to bringing these two ring salt complexes into commercial production as humidity sensors. R&D has continued essentially uninterrupted since then, growing in breadth and depth. It was found that the unmodified benzophenone salts were flawed for use as sensors. Thus, pioneering work was necessary to develop methods of stabilizing the salt complexes with the polyvalent metals $Cu^{++}$, $Ca^{++}$, $Ba^{++}$ and many others as well as with polymers. This first phase, the benzophenone salt phase, resulted in my securing the following patents on the materials and their applications: U.S. Pat. Nos. 3,776,038, 3,863,502, 4,166,891, 4,175,207, and Canadian, British, German, and Japanese equivalents.

By the 1980's the benzophenone materials had advanced to the place where they were favorably received. However, a doubled humidity range was stated to be essential for world wide commercial and industrial meters and controls. The new materials would have to have the basic properties of the benzophenone salts but, unlike the benzophenones, would have to be susceptible to molecular engineering so as the expand the sensing range.

A newly conceived R&D program was launched. It appeared at first that the benzophenone structure, limited as it was, was unique. Finally a novel two ring salt complex formed by potassium benzoylpropionate was discovered to form highly superior liquid crystals. The complexes of the salt with polymers such as the acrylates and with polyvalent metals such as copper also were superior. The other alkali metals performed similarly. Alkylation of the aroyl group was discovered to give close control over the affinity of the salt complex for water, critical in manufacturing and in use. Thus, a family of novel analogs and homologs emerged which gave sensors having a doubled humidity range. They were claimed in a Dislosure Document and were the foundation for U.S. Pat. Nos. 4,975,249 and 5,082,588.

Continued R&D expanded the materials claimed to include the aroyl salt complexes of the additional metals $Tl^+$, $Ag^+$, and $Sr^{++}$. These were claimed and included in the same disclosure document as covered the discovery of the lytotropic liquid crystal salt complexes themselves.

As work continued, in a Disclosure Document I claimed as electrical conductors and superconductors the alkali metal salt complexes of various aroyl acids alone, complexed with the alkali metal polymeric acrylates, and with polyvalent metals such as $Cu^{++}$. Further, I claimed the use of anhydrous systems using non-aqueous ligands to create "polymeric solid electrolytes" for batteries. From this ongoing research has emerged U.S. Pat. Nos. 4,975,249, 5,022,045, and 5,082,588. As noted earlier, there are copending applications as well.

Continued research and development has provided still other novel aspects of the present invention. A number of ways to usefully modify the central structures by appropriate covalent reactions have been discovered. These enhance the utility of the materials as polymer electrolytes, as electrical superconductors, as components of static dissipative plastics, etc. Such applications, of course, are based on the ability of ions or electrons to flow with ease through these salt complexes or the complexes which they form with other materials.

These new developments have been especially challenging because of the need to enhance conduction while providing methods for improving the physical properties to meet the demanding needs of the industrial world. The developments noted, however, meet many of these challeges identified long ago.

Work over the years has suggested to me the need for planar molecules having conjugated unsaturation for organic superconductors. In this application I disclose novel modes of producing yellow and orange acrylate polymers as well as deep crimson monomeric and polymeric isocyanate derivatives. These new complexes, with their greater electron mobility, offer many possibilities where less conjugated systems were effective in the past. The polymeric forms are inherently tougher and more durable, of course, than the monomeric forms. However, the latter can be modified in various ways to improve physical qualities.

In superconducting materials the need to move electrons over great distances is a key factor since molecular orientation and electron flow within a single polymer chain or crystal is of little consequence. Orientation of the molecules, which are to somehow move the electrons, must continue over vast distances in terms of molecular dimensions. Over the decades some progress has been made in this field. However, the conducting molecules, in general, have been present in standard organic crystals which could not be readily aligned. These offered severe discontinuities to electron flow at the myriad crystal boundaries. Thus, my discovery of special lyotropic liquid crystal complexes whose liquid crystal structures were oriented automatically over great distances offered a unique solution to the discontinuity problem and made macro-superconductivity a possibility.

Throughout the world a major emphasis has been placed on the development of electrical superconductors. However, there is a parallel property found in my systems which has not been emphasized elsewhere because the practical, electrically superconducting materials developed were metals or metal oxides. This parallel property is thermal non-conductivity.

It is true of superconducting materials in general that the ability of a particular material to conduct heat becomes quite low as the material reaches its critical temperature and superconductivity begins. That is, an electrical superconductor tends toward becoming what might be termed a "superinsulator" as the temperature reaches the critical level and is cooled below it. The relationship is not a simple one and varies from one material to another. However, the effect is important because of the economics of operating superconducting systems.

If the thermal conductivity of copper metal were assigned the value of 10,000, the comparable conductivity of copper oxide would be about 20 and that of many plastics about 1. If the plastics were foamed the number would drop much lower. Thus, even ordinary plastic foams are quite good insulators at cryogenic temperatures. This is very important industrially because of the high cost of first liquifying helium, nitrogen, and such gases and then maintaining them at a very low temperature for extended periods. Thus, my polymeric materials, when compounded as plastics and especially plastic foams, have the potential to provide unusually good cryogenic insulation as well.

I now have substantially improved both the monomeric and polymeric materials of my invention to maximize opportunities for molecular engineering. In electron and ion flow in oriented ring, liquid crystal systems, the space between parallel, stacked rings and the stereochemistry of the individual, oriented, planar molecules is very important to the electron or ion movement. My monomeric liquid crystal molecules automatically assemble and align in space. Thus, they offer many opportunities for varying ring spacing and position through varying the readily modified molecular structure. In contrast, with liquid crystal polymers the spacing between the planar rings disposed along the spine of the polymer is fixed. Nevertheless, in the polymeric form there is the advantage that the liquid crystal phase is generally broadened and stabilized.

These differences between polymeric and non-polymeric complexes is why access to both is desirable for optimization of a system to meet a particular need. Further, the coordination of my monomeric liquid crystal complexes along the chains of linear, liquid crystal polymers permits still additional molecular engineering. Though the spacing of the groups pendant along the polymer's spine is fixed, the steric orientation of the groups can be modified by the molecular structure of the metal complexes coordinated with them.

The lyotropic liquid crystal complexes of my U.S. Pat. No. 5,082,588 are formed through coordination chemistry. An electron donor ligand transfers electrons to an acceptor such as a metal cation. The novel materials of this present application involve both coordination and covalent chemistry. However, of course, once coordination compounds involving electron transfer have formed, there is no difference in kind between these and those having ordinary covalent bonds.

Though the salt complexes of my invention are of great importance, so are the non-polymeric and polymeric ligands which may be coordinated with them in various ways to enhance electronic and ionic conduction, to control physical properties, etc. That the complexing polymers are of great importance was established early in my work. That the accompanying metal ions incorporated in my "triad" systems of salt complex/polymeric ligand/nonpolymeric ligand, for example, also are of very great importance should be emphasized as well. This is because the ions tend to equilibrate among the various components of these systems. Thus, to further improve my materials, I have developed novel, improved polymers and improved sources of both monovalent and polyvalent ions to give more latitude in the application of these materials.

In my copending application I established triad combinations. These were three materials which allowed dissolution and which gave great flexibility in the use of the materials. Anhydrous, concentrated solutions of my salt complexes could now be made. This was of great importance because of the many potential applications and the limited solubility of the salt complexes when used alone in non-aqueous solvents.

The present invention provides novel ways to substantially improve the properties of a number of commercial polyamides and, especially, liquid crystal type, aromatic polyamides, by building on my triad systems. These lyotropic polymers, often designated as aramids, yield liquid crystalline solutions because of inherently rigid chains. The chain is produced by aromatic units with coaxial or parallel and oppositely extending bonds combined with the partial double bond character of the C—N bond in the predominantly trans amide linkage. Materials such as poly(1,4-benzamide) and poly(-phenyleneterephthalamide) illustrate the type.

In the standard manufacture of such polymers they are put into solution in appropriate, specialized solvents in such concentrations as to form liquid crystal phases for further processing. A frequently used solvent for the aramids consists of lithium chloride or calcium chloride dissolved in an amide solvent such as dimethylformamide (DMF) or dimethylacetamide (DMAC). Tetramethylurea (TMU), 1-methyl-2-pyrrolidinone, and other NCO-type ligand solvents (such as I have listed in my copending application Ser. No. 07/642,009 where triads are discussed) also can be used alone or in admixture.

The metal chlorides are believed to align along the chains and so solubilize them and make further processing possible. After various manufacturing steps are completed the metal Chlorides then are carefully washed out of the fibers or granules of the liquid crystal polymer because of the great corrosiveness and hygroscopicity of these halides.

In my U.S. Pat. No. 5,082,588 I claim the alkali metal salts of special aroyl acids complexed with polyamides, among the polymers claimed. In my copending application Ser. No. 07/642,009 I describe novel triads formed from the complexation and solution of (a) polyamides (or other polymers) along with (b) my aroyl salts, and (c) non-polymeric solvent ligands such as dimethylacetamide (DMAC). This same novel process can be used to solubilize the aromatic polyamides to create novel polymer complexes having improved electrical conductivity, for example.

Instead of using lithium or calcium chloride and DMAC to dissolve the aromatic polyamide, my lithium and calcium aroyl salt complexes and DMAC are used. By choosing an appropriately alkylated aroyl group there is no problem with hygroscopicity or corrosiveness in the final polymer/salt complex. Typically, 3% of lithium chloride may be used to solubilize 20% of a polymer such as poly(1,4 benzamide) in DMAC. To offset the higher molecular weight of the lithium aroyl salt complexes, the inorganic chloride may be used in conjunction with the organic complex to secure the desired solubilization at a lower concentration of the organic complex and thus a lower cost.

As useful as my triads are, I have found that there are applications where an unusual challenge is posed by the need to not only dissolve my salt complexes but to distribute them in small, controlled amounts throughout plastic systems. Preferably this is done without the burden of having to dissolve the plastic in which my salt complexes are to be dispersed. This problem is met in creating static dissipative polymers, EMI-control plastics, and other large volume applications.

For such applications the use of supercritical fluids, and especially supercritical carbon dioxide, is of great value since it allows my materials, dissolved in the supercritical fluid, to readily diffuse throughout a variety of plastics. With carbon dioxide, of course, there are no toxic or expensive solvents to remove after processing. Only a reduction of pressure and venting of the gaseous carbon dioxide is required. In some cases the salt complexes need not be put into triad-solubilized form, for the "plain" salt complex without special solubilization processing dissolves into the supercritical fluid and into the plastic particles through a steady displacement of equilibrium.

Turning to the specifics of the improvements and discoveries which I have generally described, they have been built around the key structures of the special aroyl acids I have developed with which to to prepare the liquid crystal salt complexes of ray U.S. Pat. No. 5,082,588. It is their unique structure, with its special balance of polar forces, which causes the oxygenated salt chains to form second rings and thus make possible liquid crystal formation, with the unique features which the liquid crystal (LC) phase makes possible.

One preferred embodiment of this invention centers on the discovery of novel covalently bonded, liquid crystal polymers of my special aroyl salt complexes, which until now I have used in their non-polymeric form. The polymeric salt complexes assist in the effective use of non-polymeric forms previously used.

It should be emphasized that the covalent bonding characteristic of the polymers in no way reduces the importance of the products of coordinate bonding which copending applications particularly address. Rather, materials bonded covalently complement those formed through coordinate bonding and, in many instances, a final complex is the result of using both covalent and coordinate bonding in it preparation.

To clarify this key point, it is helpful to recall that typical "triads," such as I disclose in my copending application Ser. No. 07/642,009 generally include (a) an alkali metal salt of my special aroyl acid, either saturated or unsaturated [R—Aryl—CO—X—(CH$_2$)$_Y$—CO$_2$H], (b) a non-aqueous, non-polymeric ligand solvent that forms a coordinate bond with the metal of the metal salt(a), and (c) a polymeric ligand that is a polymer containing repetitive oxygen groups along a substantially linear chain that form coordinate bonds with the metal ions of metal salt (a). The polymeric ligand of (c) has been a non-liquid crystal, commercial polymer until now in my complexes. I now replace it with a covalently formed copolymer of an unsaturated acid and its metal salt of the aroyl acids used to prepare the salt complex (a) of the triad mentioned. The ligand solvent (b) can be a-monofunctional, coordinating ligand such as DMAC. Or it can be a polyfunctional ligand solvent such as an isocyanate which has solvent powers but which can also covalently react with the free carboxyl groups of my acid copolymers to cause cross-linking. It can be a combination of the two types as well.

My salt complexes are based on both saturated and unsaturated acids. It is the latter, of course, which I have polymerized to form liquid crystal polymers. I have prepared both homopolymers and corresponding copolymers of unsaturated aroyl salts and acids such as methylbenzoylacrylic acid. These may be used in a triad such as I have just described with both the polymeric ligand (c) and the non-polymeric salt ligand (a) based on my special aroyl acids. Or the polymer ligand (c) may be used without the salt ligand (a) in combination with the non-polymeric ligand (b) in what might be termed a "diad."

The formation of a diad such as this is of special interest. It could consist, for example, of an alkali metal polymer of one of my unsaturated aroyl acids, such as methylbenzoylacrylic acid, and a non-polymeric ligand solvent such as dimethylacetamide (DMAC) and/or N-methyl-2-pyrrolidone. It can function for some applications as though it were a triad. This is because the polymer itself already has present in a self-contained unit both salt complex groups and aryl groups covalently bonded and disposed along the polymer chain in an oriented way.

In a typical triad, the salt complex group and aryl group are part of each salt complex molecule, of course. The complexes are attached with coordinate bonds to oxygen groups along the chain of a separate, standard polymer. In what might be termed a "super-triad," both the salt ligand (a) and the polymeric salt ligand (c) are based on my special aroyl acids and both covalent and coordinate bonding are important.

Such a preferred embodiment of a "super-triad" lyotropic liquid crystal salt complex comprises:

(a) A lyotropic liquid crystal aroyl salt ligand as previously defined;
(b) A non-aqueous, non-polymeric ligand solvent such as an isocyanate and/or amide; and
(c) A polymeric ligand that is a polymer having repetitive oxygen groups along a linear chain, such as an acrylic copolymer of an aroylacrylic acid and an alkali metal salt of an unsaturated acid (such as benzoylacrylic acid) used to prepare the salt complex ligand (a).

Though I do not wish to be bound by theory, I believe that the powerful orientation effects observed are caused by the special dual ring structure which characterizes my complexes. Solutions of ordinary polymeric metal acrylates readily dry to form films which show no liquid crystal birefringence when viewed through crossed polarizers. In contrast, when my polymeric alkali metal aroylacrylates, for example, are deposited in film form, through controlled evaporation of excess DMAC ligand, the films are birefringent. It is theorized that this is because the phenyl rings (attached to my oxygenated rings) tend to orient with respect to other phenyl rings to form what might be termed a "ring corridor." Concurrently, in the spontaneous process of the alignment of the phenyl rings and their pi-electron clouds with one another, the oxygenated rings and their cations are assembled in a "metal/ring plane" since the two rings are attached to one another, though flexibly.

It should be noted that the polymers, with their covalently bonded, repetitive aroyl structures along the stiff spine, have fixed spacing between the repeating groups. Thus, the whole structure tends to broaden and stabilize the liquid crystal phase, an advantage. However, liquid crystal systems based on my non-polymeric, aroyl salt complexes are valuable too. They offer greater opportunities for varying the spacing and orientation between the individual, aligned molecules through selection of the polymer with which to form coordinate bonds. Thus, it is expected that access to both polymeric and non-polymeric materials will provide the desired opportunity for optimization of system characteristics with regard to ion or electron movement.

The polymeric ligand used can be a homopolymer of an alkali metal salt of an unsaturated acid such as benzoylacrylic acid, as noted. However, the use of a copolymer having a carefully controlled number of free carboxyl groups along an acrylate chain consisting largely of alkali metal carboxylate groups has important advantages. It allows the use of a polyfunctional, non-aqueous isocyanate, for example, to tie the copolymers together through reaction at the carboxyl groups. Covalent cross-linking with such isocyanates as p-phenylene diisocyanate (PPDI) allows the development of superior physical properties. Such isocyanates, to be used for cross-linking, can be of the so-called "blocked" type for convenience in application, and they will be discussed later. Cross-linking agents such as diphenylmethane 4,4'-diisocyanate (4,4'MDI), Polymeric MDI, and others can also be used.

Turning to the preparation of aroylacrylate polymers, either cis or trans form of benzoylacrylic acid polymerizes satisfactorily. The preparation of the acids is readily accomplished using the Friedel and Crafts reaction.

PREPARATION OF TRANS -3-(4-BENZOYL)ACRYLIC ACID

To a mixture of 200 ml of anhydrous, thiophene-free benzene and 49 gm (0.5 moles) of maleic anhydride at room temperature, 132 gm (1 mole) of aluminum chloride (J. T. Baker, granular, anhydrous C.P. grade) is added in small portions. The reaction temperature rises to 40°–45° C. and is maintained at this level during the addition. Then the reaction mixture is heated on a steam bath for 2 to 3 hr, cooled rapidly and added to an excess of ice and 1:1 hydrochloric acid. The benzene layer is separated and freed of benzene by steam distillation. On cooling, the supernatant liquid is decanted from the semisolid residue. The crude product is dissolved in 5% sodium carbonate solution, filtered, and acidified with efficient cooling. The precipitating solid is washed with cold water and dried. Yields as high as 91% have been obtained. The product, recrystallized from water, forms a colorless hydrate, m.p. 60°–62° C. Recrystallized from benzene (with minimum heating period) the anhydrous product, m.p. 94°–96° C. is obtained.

The polymerization of the aroylacrylates is readily accomplished by standard methods since the acids fall into the class of Maleic/Fumaric Dienophiles, having both a carboxyl and a keto activating group. There is a vast body of literature describing the preparation of acrylic polymers of many types. However, in the excellent book, *Polymer Synthesis,* Vol II, S. R. Sandler and W. Karo, Academic Press, Inc., New York, 1977, p.264, the chapter, "Polymerization of Acrylic Acids and Related Compounds," describes in detail the aqueous and non-aqueous polymerization of homopolymers of acrylic acids and acrylate salts and of copolymers, using various initiators.

The following example of the preparation of the copolymer, acid lithium methylbenzoylacrylate, typifies a method which provides excellent polymers. It is often desirable to use more than a single acid, as well as more than a single metal, in the preparation of the polymers so as to modify liquid crystal formation.

EXAMPLE 1

To prepare the acid lithium acrylate copolymer, 4.85 g (0.025 mole) of 98% pure trans-3-(4-methylbenzoyl) acrylic acid was slurried in 20 ml distilled water in a heated beaker with a mechanical stirrer. Stirring constantly, at 80° C. the acid was 95% neutralized with 11.88 ml 2N lithium hydroxide solution. The solution was digested until free of particles and then filtered, the volume adjusted to 40 ml and transferred to a flask with a reflux condenser, thermometer, and mechanical stirrer. The solution was heated to 90° C. and 10 ml of a solution of sodium persulfate (0.01 g/ml) was added with constant stirring. The batch was held at 90° C. with constant stirring for 30 minutes. A viscous, orange-colored solution resulted. It was vacuum dried at 20° C. to avoid the cross-linking which thermal processing can cause with some acrylates. The dried acid lithium aroylacrylate co-polymer was powdered in a mortar and pestle, sieved to 100 mesh for further reactions, and held over silica get to maintain its dryness. Other metals, including the other alkali metals alone or as mixtures and $Ag^+$ can be substituted to provide good results.

The dried, powdered polymer readily dissolved in hot DMAC. On coating a glass slide with the solution and slowly evaporating excess DMAC in a hot air stream while viewing the material through crossed polarizers (Polars), a birefringent liquid crystal film formed. This is an example of the "diad" referred to before.

EXAMPLE 2

To prepare what I referred to before as a "super-triads" I coordinately bond a liquid crystal coordination complex of one of my metal aroyl salt complexes and the covalently bonded lithium aroylacrylate/aroylacrylic acid copolymer of Example 1. Thus, 0.49 g (0.0025 mole) of the powdered lithium copolymer complex was dry mixed with 0.46 g (0.0025 mole) of powdered lithium hippurate. 10 ml DMAC was added and the mass heated in a beaker with stirring at 110° C. The solid complexes dissolved to form a clear solution. On careful evaporation of excess DMAC from a film of the triad on a glass slide, a bright, birefringent, liquid crystal film formed. This is the product formed as the metal of the hippurate coordinated with the oxygen groups of the aroylacrylate polymer in the presence of the DMAC coordinating ligand solvent.

EXAMPLE 3

To prepare the acid thallium acrylate copolymer, 4.85 g (0.025 mole) of 98% pure trans-3-(4-methylbenzoyl) acrylic acid was slurried in 150 ml distilled water. This was in a flask fitted with addition funnel, reflux condenser, thermometer, and mechanical stirrer, all in a hood. 5.57 g (0.0119 mole) of thallous carbonate (EXTREMELY POISONOUS) was carefully, quickly added to neutralize 95% of the available carboxyl groups. Great care was taken to avoid escape of dust or spray created by the carbon dioxide released as the carbonate reacted with the acid. The temperature was raised to 80° C. with constant stirring, and stirring continued until gas bubbling ceased and no particles of acid could be seen.

The volume was adjusted to 190 ml with distilled water and 10 ml of a solution of sodium persulfate (0.01 g/ml) was added with constant stirring. The batch was heated to 90° C. and constant stirring continued for 30 minutes. The resulting polymer solution was vacuum dried at 20° C. to avoid crosslinking, which thermal processing can cause with some acrylates, and held over silica gel to maintain dryness.

A water solution of the polymer allowed to dry on a glass slide formed a bright, birefringent, incipiently liquid crystal film, suggesting that the optimization of molecular weight would enhance its liquid crystal orientation.

EXAMPLE 4

To prepare the acid barium acrylate copolymer, 4.85 g (0.025 mole) of 98% pure trans-3-(4-methylbenzoyl) acrylic acid was added slowly to 150 ml carbon dioxide-free, well boiled, distilled water at 80° C. in which 2.04 g (0.0119 mole) of anhydrous, carbonate-free, barium hydroxide had been dissolved. This was in a flask with a reflux condenser, thermometer, and mechanical stirrer. The stirring was continued until all of the acid particles had dissolved.

The volume was adjusted to 190 ml with distilled water and 10 ml of a solution of sodium persulfate (0.01 g/ml) was added with constant stirring. The batch was heated to 90° C. and constant stirring continued for 30 minutes. The resulting polymer solution was vacuum dried at 20° C. to avoid cross-linking, which thermal processing can cause with some acrylates, and held over silica gel to maintain dryness.

A water solution of the polymer allowed to dry on a glass slide formed a bright, birefringent liquid crystal film. Other metals including $Ca^{++}$, $Sr^{++}$, $Pb^{++}$, $Sn^{++}$, $Cu^{++}$, $Ni^{++}$, $Y^{+++}$, $Bi^{+++}$, $Gd^{+++}$, $Nd^{+++}$, $Yb^{+++}$, $La^{+++}$, $Sc^{+++}$, and $Sn^{+++}$ can be substituted to provide good results.

The same general methods can be used to prepare homopolymers of the aroylacrylates by first neutralizing the solution of the monomeric salt with an appropriate base so as to bring the pH to 9.0. However, as noted before, the acid acrylates are often desired so that the free carboxyl groups can be reacted with appropriate cross-linking reagents so as to develop structures of enhanced physical properties for industrial and commercial applications. In the two following examples, polyfunctional isocyanates are used for cross-linking, the first being difunctional and the second having a functionality of 8-10.

EXAMPLE 5

To cross-link an acid polymeric salt complex such as is desired in Example 1, the 5% of free carboxylic groups is reacted with difunctional diphenylmethane 4,4' diisocyanate (4,4' MDI). Thus, 4.90 g (0.025 mole of the acid salt, containing the equivalent of 4.66 g, or 0.0237 mole, of normal lithium aroylacrylate, and 0.24 g, or 0.0013 mole, of the aroylacrylic acid) of the acid lithium salt complex of Example I was slurried in 95 ml dimethylacetamide (DMAC) in a flask fitted with an addition funnel, reflux condenser, thermometer, and mechanical stirrer. 0.16 g (0.0006 mole) MDI dissolved in 5 ml DMAC was added and the batch heated to 115° C. with constant stirring. Stirring was continued for 30 minutes to dissolve the salt and react the MDI with the free carboxyl groups.

On controlled evaporation of excess DMAC from a film of the material on a glass slide, it formed a birefringent liquid crystal film when viewed between crossed polars.

To further extend the cross-linking, an oligomer of MDI industrially designated as Polymeric MDI, is useful. It has a functionality of 8-10 as manufactured for use in polyurethane but its functionality can be increased.

EXAMPLE 6

The situation with an oligomer is similar to that met in Example 5 except that the molecular weight of the isocyanate is different. In a typical commercial material the "isocyanate equivalent weight" is 141.9. Thus, 0.18 g (0.0013 mole) of the Polymeric MDI is needed for cross-linking rather than the 0.16 g of Example 5. The same reaction equipment and conditions were used.

On controlled evaporation of excess DMAC, a film of good birefringence and liquid crystal nature formed. The film was tougher than that produced using MDI.

I have focused first on the use of acid copolymers synthesized from precise quantities of my unsaturated aroyl acids and their salts. This is because these acid copolymers are quite different from the materials secured by partial post-neutralization of homopolymers of my unsaturated, aroyl acids. The latter inherently have non-reproducible characteristics.

In my patents I have not polymerized my own alkali metal acrylates. Rather, I have used commercial acid polymers and neutralized them in the presence of my special aroylacrylate salts and polyvalent metal ions such as $Cu^{++}$. This is because the quality control required for commercial humidity sensors is quite different from that required for polymer electrolytes, superconductors, etc. This is because the sensors operate within a protected enclosure, never touched, where cross-linking is needed only to prevent deliquescent flow. Precisely reproducible cross-linking to produce films consistently of great toughness, neither too soft nor brittle, is not required. In contrast, electrically conducting circuitry, for example, must have highly superior physical characteristics for use in the industrial world where maintenance is routine.

Turning to some of the reasons for the subtle major differences between the copolymers and the post-neutralized homopolymers, the economics of commercial manufacturing prevents highly dilute polymer solutions being used. When one attempts to neutralize polymeric acrylic acids at acceptable concentration levels, the molecules expand. The viscosity of the solution increases dramatically, reaching a point at about 80% of neutralization where it is often several hundred times its original viscosity. Concurrently, "site binding" of cations occurs, the cations behaving as though bound in place in the polymer structure because of the strong electrostatic forces surrounding regions of the chains bearing many ionized carboxyl groups. As a result of these two factors, high viscosity and site binding, neutralized polymeric acids have serious micro-heterogeniety problems, even when very slow neutralization and long equilibration is practiced. In attempts to minimize these serious problems, very high shear mixing equipment has been tried during neutralization. It has been found that the high shear rate brings scission of the polymer molecules, changing the polymer's structure entirely and only partially reducing heterogeneity.

There is still another problem with neutralizing the acid polymer. There is a great tendency for a substantial and somewhat variable amount of monomeric acid to remain in such homopolymers. The monomer, left from a Gaussian distribution of molecular weights at the end of polymerization, cannot easily be vacuum stripped from the polymer. This is because of the inherently low vapor pressure of the aroyl monomers and the strong tendency for the acids to form hydrogen bonded dimers.

Thus, though I claim both modes of producing acid polymers for cross-linking, they are separate methods and the products produced are importantly different. This also is especially true of the cross-linked products which are produced when their carboxyl groups are cross-linked, for it is well accepted that cross-linking is a very sensitive process.

It is desirable to be able to widely vary the physical properties of the final, cross-linked polymeric structure. Thus, I claim for each of these two modes of producing acid polymers the use of from approximately 1 to 30% of free carboxyl groups in the acid polymer, Usually from 5 to 10% gives suitable properties.

Having noted these key differences and some of the reasons for them, my next example covers the preparation of the acid homopolymer, the base material to be neutralized to the desired degree.

EXAMPLE 7

To prepare the homopolymer of methylbenzoylacrylic acid, 4.85 g (0.025 mole) of 98% pure trans-3-(4-methylbenzoyl) acrylic acid and 0.02 g (0.00007 mole) of benzoyl peroxide were added to 25 ml anhydrous toluene. With suitable protective devices the mixture was carefully heated in a thin-walled, mechanically stirred vessel provided with an explosion-proof motor and a water jacket for heating/cooling for rapid removal of heat when the exothermic polymerization reaction begins. The jacket temperature was carefully brought to 80° C. and the temperature held there for 30 minutes and then cooled to room temperature.

The polymer was purified by very slowly adding the polymer/toluene batch to 150 ml cold hexadecane mechanically stirred at a high rate using an explosion-proof motor. The precipitated polymer was filtered from the solvents, washed with hexadecane, and vacuum dried.

"Pechmann Dyes," colored, unsaturated acids obtained when benzoylacrylic acids are heated with dehydrating agents [reviewed by Bogert and Ritter, *Proc. Natl. Acad. Sci.*, U.S., 10, p. 363 (1924)] can be processed in the same general way to obtain materials having more extended conjugated double bonds than the acrylates offer.

I have discovered other important embodiments of my invention. These are novel reaction products of my salt complexes having increased conjugated unsaturation. They can be described as products formed by covalent addition of:

(a) An unsaturated, lyotropic liquid crystal salt complex as previously defined, and (b) An aromatic isocyanate or isothiocyanate.

The aromatic isocyanate or isothiocyanate can be monomeric or "polymeric." A liquid solvent such as DMAC can be used to assist in solubilizing the salt complex for optimum reactivity, controlling the reaction, and putting the reaction product(s) into a convenient form for use.

For optimum engineering of superconductors, polymer electrolytes, static dissipative plastics, etc. it is highly desirable to have available a variety of different monomers and polymers. This is because the needs of these systems vary greatly. Some need an ion flow with little electron flow and others the opposite. My discovery of a process for covalently modifying the unsaturated salt complexes of my invention (so as to give an improved electron mobility in the molecular structure) is an important advance. The increased conjugated unsaturation and corresponding electron flow is accompanied by a shift from pale yellow to deep crimson at the moment that my salt complexes are covalently modified.

Further, as an extension of the chemistry of the metal complexes, I have found unexpectedly that non-metallic cations such as quaternary ammonium and phosphonium form salts of the unsaturated acids of my U.S. Pat. No. 5,082,588. They also can be reacted with isocyanates to form unsaturated dyes. For example, tetramethylammonium hydroxide forms a salt with methylbenzoylacrylic acid which reacts further with Polymeric MDI in DMAC to form a deep crimson, soluble reaction product.

The unexpected addition reactions of the metal salt complexes are rapid and complete and so versatile that all of my metal salt complexes respond in the same way and with essentially the same rapidity. The double bond of the metal acrylates appears to react on a one to one basis with the double bond of the isocyanate group.

The brilliant crimson color of these novel reaction products—lyotropic liquid crystal, polymeric and non-polymeric complexes—leads me to theorize that dipolar ions or inner salts form, similar to those believed to exist in Quinoline yellow. Thus, an extended, conjugated, double bond network is believed to form, involving the double bonds of the phenylene group of the isocyanate section of the complex as well as the double bonds of the aryl group of the original metal aroyl complex. These, of course, are connected by intervening double bonds.

Because of the size of the polyurethane industry a wide variety of aromatic isocyanates are available. These range from a simple monofunctional one such as phenylisocyanate, to a non-polymeric but difunctional one such as 1,4 phenylene diisocyanate, to what is considered to be a dimer diphenylmethane 4,4' diisocyanate (4,4' MDI). There are also oligomers containing 8 to 10 or more pendant NCO groups along a polymethylenepolyphenylene chain. The use of compounds such as 1,5 naphthalene diisocyanate, naphthalene monoisocyanate, and the isocyanates of even larger ring structures such as anthracene, pyrene, perylene, etc. to react with my metal aroyl acrylates, allows access to extended, conjugated, unsaturated systems. The selection of isothiocyanates is much more limited.

An example of the type of reaction secured with a relatively simple isocyanate is that of 4,4' MDI, a large volume material in the polyurethane industry, and lithium methylbenzoylacrylate.

EXAMPLE 8

To prepare the reaction product of lithium benzoylacrylate and 4,4' MDI, the salt complex was made first by drying in an oven at 80° C. 20 ml of a 1M solution (0.02 mole) of the salt which has been neutralized to pH 8.8 using a glass electrode. The dried salt was powdered in a mortar and pestle, screened to 100 mesh, redried at 80° C. for one hour, and bottled. Though a processed, liquid form of 4,4' MDI is available, BASF's Lupranate M, a crystalline form containing 98% of 4,4' MI)f and 2% of mixed isomers of MDI was used. Each molecule of this material, of course, bears two NCO groups.

A flask fitted with an addition funnel, reflux condenser, thermometer, and mechanical stirrer was charged with 35 ml DMAC and then with 0.75 g (0.003 mole) 4,4' MDI. The DMAC was heated to 110° C. and 1.18 g (0.006 mole) powdered lithium methylbenzoylacrylate was added with constant stirring. It reacted rapidly and completely to form a clear, soluble, deep crimson product. On evaporation of excess DMAC from a film of this material on a glass slide, it formed a dimly birefringent liquid crystal display between crossed polars. Orientation in such large sterically complex molecules is difficult.

On adding 1.18 g (0.006 mole) of dried, powdered lithium methylhippurate to the batch it readily dissolved at 110° C. with stirring to form a clear red coordination product. This complex formed a brightly birefringent liquid crystal film on evaporation of excess DMAC. Depending on the application, the ratio of salt complex added later to coordinate with the metal acrylate/MDI reaction product can be widely varied, of course.

I particularly claim the general reaction of the aromatic isocyanates with my unsaturated salt complexes, as well as the many novel reaction products which can be produced using it. The reaction is distinguished by its speed and completeness, the ease of carrying it out, the high degree of conjugated unsaturation produced, and the stability of the resulting ring structures. These reaction characteristics are believed to be due to the activating positions of my keto and carboxylate groups with respect to the double bond. Further, it is theorized that the ring structure of the hydrophylic, oxygenated group, created by the metal of the carboxylate group coordinating with the keto group, is important in the activation.

I have discovered that the reaction products of "Polymeric MDI" also are of major importance. Typically, the production of 4,4' MDI starts with the condensation of aniline and formaldehyde. After further reactions both 4,4' MDI and Polymeric MDI are produced concurrently. Chemical Abstracts terms the "polymeric" material "isocyanic acid, polymethylenepolyphenylene ester." It consists of low molecular weight oligomers with a functionality of from 8 to 10. It is also known as polymethylene polyphenylene isocyanate.

It is important to note that "Polymeric MDI" is a polymer in the sense that repetitive parts or "mers" are present. These are the connected methylenes and phenylenes of the Chemical Abstracts name. However the pendant isocyanate groups along the "polymeric" chain are monomers in every sense of the word, ready to react individually as monomers do. This is a key point.

Usually 4,4' MDI is distilled from the oligomers to leave an oligomer content ranging from 30% to as high as 82%. When such a mixture of MDI and higher oligomers is reacted in the 1:1 molar ratio (NCO double bond:salt complex double bond) as was used before, the same rapid and complete reaction occurs.

EXAMPLE 9

So as to compare the reactions of 4,4' MDI and Polymeric MDI, lithium methylbenzoylacrylate from the same batch prepared for use in Example 8 was used. It was prepared in the same way as before. This time Polymeric MDI (PAPI20 from Dow Chemical Company) containing 75-82% of Polymeric MDI and 25-18% MDI was used as the isocyanate source.

It had a viscosity of 1841 cps and an "isocyanate equivalent weight" of 141.9. Thus, 0.85 g (0.006 mole) of the PAPI20 was reacted with 1.18 g (0.006 mole) of the lithium salt in the same equipment and in the same way as before. Again the reaction was swift and complete and a clear, deep crimson product resulted, the solution being more viscous than before. Other metals-,including the other alkali metals alone or in mixture, and $Ag^+$ can be substituted to provide good results.

On evaporation of excess DMAC on a glass slide this material Formed a much brighter, birefringent liquid crystal film than the product from 100% 4,4' MDI of Example 8 had. On reacting 1.19g (0.006 mole) of lithium methylhippurate with this batch it readily dissolved at 110° C. to form a clear red coordination complex. The product formed an exceptionally bright, birefringent liquid crystal film on evaporation of excess DMAC.

To optimize the orientation of the pendant, unsaturated, reaction product groups, it is highly desirable to remove the balance of the 4,4' MDI using low pressure, thin film vacuum stripping. Further, the "tars" formed during the manufacture of the polymeric isocyanates, which are not a problem in commercial foam manufacture, should be removed to allow rapid and complete orientation of the molecules for optimum liquid crystal formation. The detarring can be accomplished through a combination of the use of activated charcoal, activated earths, and solvents of differential solubility for the materials present, or through similar methods.

I have noted earlier that the functionality of the oligomers is dependent on the ratio of aniline to formaldehyde initially used. To get the highest functionality possible for these complexes, I prefer to use materials expressly made for this purpose rather than to use those prepared for the less demanding applications of the polyurethane foam field. This is because it is essential that the axial ratio of my polymers (the ratio of the length of the chain to its width) be quite substantial for the formation of a highly stable liquid crystal phase.

It is also possible to extend the isocyanate chain's length and to increase its rigidity through tying the chains together with such compounds as small, rigid, difunctional glycols. In such a case, of course, some of the isocyanate groups must be left free, unreacted with acrylate complexes so that there are groups available for the glycol reaction.

Instead of reacting my metal aroylacrylate salt complexes with Polymeric MDI from Dow Chemical Co., the same company's isocyanatoethyl methacrylate can be used. Preferably it is first polymerized. My aroylacrylate salts are then thermally reacted with the methacrylate polymer's isocyanate groups, just as I have reacted them with isocyanate groups of Polymeric MDI,to form novel methacrylate/isocyanate/aroyl complex reaction products. Analogs and homologs of the isocyanatoethyl methacrylate can be used in the same way, and the isothiocyanate group can be used in place of the isocyanate group.

The present invention also provides a number of additional metals for molecular engineering. In the development of the complexes of my U.S. Pat. No. 5,082,588, I worked extensively with a large number of polyvalent metal ions as salt complex formers. In the development, I established that the polyvalent metal salt complexes of both the aroyl acids and the polymers of the patent can be readily made and are stable. Of the many metal ions evaluated as complex formers, the number claimed was reduced to a few distinguished by their excellence in meeting the needs of the particular application. Of this group, copper proved to be truly exceptional. Now, in new uses for my complexes, such as in superconductors, copper complexes continue to maintain their position of unique importance. Thus, with the complexes of copper as essential materials, I have developed an expanded group of useful metal complexes. These include those of utility in fields such as superconductivity.

As expected, these metal complexes have been found to form ring complexes with the acids of my invention in the same way as the alkali metals do. Further, I found that the complexes which they form with the unsaturated acids of my invention, such as methylbenzoylacrylic acid, react rapidly and completely with isocyanate groups just as the alkali metal salt complexes do. Thus the coordination complexes which the non-alkali metals form, as well as the covalent reaction products which these coordination complexes form on reaction with non-polymeric and polymeric aromatic isocyanates, are valuable embodiments of my invention. The metal ions which coordinate in salt complexes and polymers of this invention are $Ti^+$, $Cu^{++}$, $Ca^{++}$, $Sr^{++}$, $Ba^{++}$, $Pb^{++}$, $Sn^{++}$, $Y^{+++}$, $Bi^{+++}$, $Gd^{+++}$, $Nd^{+++}$, $Yb^{+++}$, $La^{+++}$, $Sc^{+++}$, and $Sn^{+++}$.

In the development of improved superconductors it is desirable in many instances to optimize the performance of metal complexes by blending the organic compounds in the same metal ratios as have been found to give high critical temperatures in superconducting, inorganic metal oxides. Such a novel multi-element blend of my complexes can be used as a matrix to bond together powdered inorganic oxides which are superconductors. Thus, as examples of the preparation of my metal complexes, I have chosen the preparation of thallium, calcium, barium, and copper complexes. Inorganic oxides using these four elements have shown very high superconducting critical temperatures. In each case I describe preparing both the metal acrylate and its reaction product with Polymeric MDI.

EXAMPLE 10

To prepare thallous methylbenzoylacrylate, 2.91 g (0.015 mole) of : 98% pure trans-3-(4-methylbenzoyl) acrylic acid was slurried in 200 ml distilled water in a flask fitted with addition funnel, reflux condenser, thermometer, and mechanical stirrer, all in a hood. 3.47 g (0.0074 mole) thallous carbonate (EXTREMELY POISONOUS) was carefully, quickly added taking great care to avoid escape of dust or spray created by the carbon dioxide released as the carbonate reacted with the acid. The temperature was raised to 80° C. with constant stirring, and stirring continued until gas bubbling ceased and no particles of acid could be seen. The slightly acid salt solution was cooled and the solution carefully transferred to a beaker. The pH was adjusted to 8.8 using a glass electrode and a distilled water solution of 0.5% thallous carbonate. The neutralized batch was oven dried at 80° C. and dried form an additional two hours after it had become dry and friable.

20 ml DMAC was added to the dried salt in the beaker and the salt loosed with a spatula. The slurried mass was transferred to a flask fitted with an addition funnel, reflux condenser, thermometer, and mechanical stirrer. Another 20 ml DMAC increment was added to the beaker and the remaining particles of the thallous salt complex were loosed with a spatula. This material was then transferred to the flask. This was repeated with another 20 ml of DMAC and the slurry was heated to 125° C. with constant stirring until it had dissolved.

2.13 g (0.015 mole NCO) of the Polymeric MDI of Example 6 was added with constant stirring. A deep crimson, clear solution of the polymeric reaction product formed. This material on a glass slide formed a bright, birefringent, liquid crystal film on evaporation of excess DMAC.

EXAMPLE 11

To prepare calcium methylbenzoylacrylate, 2.91 g (0.015 mole) of the acrylic acid of Example 10 was slurried in 200 ml distilled water in a beaker fitted with a thermometer and mechanical stirrer. 0.56 g (0.0075 mole) calcium hydroxide, carbonate free, was added with constant stirring. The temperature was raised to 80° C. and stirring continued until the acid and calcium hydroxide had dissolved. The pH was adjusted to 8.8 using a saturated solution of calcium hydroxide in carbon dioxide-free distilled water. The batch was filtered and oven dried at 80° C. The dried salt complex was ground in a mortar and pestle, screened to 100 mesh, and dried another two hours.

The powdered salt complex was slurried in 50 ml DMAC in a flask fitted with addition funnel, reflux condenser, thermometer, and mechanical stirrer. The temperature was raised to 110° C. and 2.13 g (0.015 mole) of the Polymeric MDI of Example 6 was added with constant stirring. Again a deep crimson, clear solution of the polymeric reaction product formed. It was more viscous than the lithium or thallium acrylate/Polymeric MDI reaction products, presumably because of the cross-linking which the polyvalent metal ions brings. On evaporation of excess DMAC from the film of the material on a glass slide, a bright, birefringent liquid crystal array formed.

EXAMPLE 12

To prepare barium acrylate, 2.85 g (0.015 mole) of the acrylic acid of Example 10 was slurried in 200 ml distilled water and reacted with 1.29 g (0.0075 mole) barium hydroxide using the same equipment and procedures used in Example 11 to prepare the powdered salt.

The powdered salt complex was slurried in 50 ml DMAC and reacted with 2.13 g (0.015 mole NCO) of the Polymeric MDI of Example 6 using the same equipment and procedures used in Example 5. Again a deep crimson, clear, viscous solution formed. On evaporation of excess DMAC from a film of the material on a glass slide a bright, birefringent liquid crystal array formed.

Sometimes the complexes of the polyvalent metal salts of the aroyl acids of my U.S. Pat. No. 5,082,588 are best formed by a metathetic reaction between a soluble alkali metal salt of a particular aroyl acid and an appropriate, soluble metal salt. The materials can be dissolved in water, methyl or ethyl alcohol, or other solvents, the insoluble metal complex being filtered from the soluble reaction products. In other cases, as in my copending application, Ser. No. 07/821,084, I react the alkali metal salt complexes of my aroyl acids metathetically with various reactive metal oxides in an anhydrous ligand solvent. However, it is often advantageous to "fuse" the appropriate aroyl acid with the oxide, hydroxide, carbonate, isopropoxide, or, sometime, acetate of the desired metal in an aqueous or non-aqueous medium.

In the example I have just given, metal carbonates and hydroxides have been reacted with an aroyl acid in water to secure the desired complex on drying. The next example illustrates the use of the fusion method using a metal hydroxide, the aroyl acid, and a non-aqueous ligand. The method was selected because it may be desired on some occasions to completely dissolve superconducting metal oxides or their non-heat treated precursors to prepare a reaction product to be used as a binder in compounding inorganic superconducting powders. Separate oxides in the correct ratio may be digested concurrently if desired.

EXAMPLE 13

To prepare cupric methylbenzoylacrylate, 2.85 g (0.015 mole) of the acrylic acid of Example 10 was digested with 0.73 g (0.0075 mole) copper hydroxide in 50 ml DMAC at 11.5° C. for three hours in the same equipment used in Example 5. A clear, deep blue-green solution formed. To the solution 2.13 g (0.015 mole NCO) of the Polymeric MDI of Example 6 was added with constant stirring. The solution rapidly became a very dark color, though it remained clear, and the viscosity increased. On a glass slide the material formed a bright, birefringent liquid crystal film on evaporating excess DMAC. Other materials including $Sr^{++}$, $Pb^{++}$, $Sn^{++}$, $Y^{+++}$, $Bi^{+++}$, $Gd^{+++}$, $Nd^{+++}$, $Yb^{+++}$, $La^{+++}$, $Sc^{+++}$ can be substituted to provide good results.

By generating my salt complexes in situ in and on superconducting metal oxide particles, my present invention provides a novel solution to a problem identified long ago but which has not been solved. The current-carrying limitations of high critical temperature superconductors can be attributed in substantial measure to the "weak link" between adjacent crystals of the superconducting oxides. Each crystal conducts electrons without resistance when cooled, but the crystal interfaces conduct much less efficiently. The interstices between crystals, depending on their dimensions and the gas molecules sorbed there, can cause still greater difficulties. Thus, a suitable matrix of the right composition and characteristics which molecularly wets the crystal faces has the potential for profoundly changing the current carrying capacity of a system.

In the in situ method, the fusion procedure is used with oxide superconductors having reactive surfaces and carried to such a degree as to only partially dissolve the oxide particles. When the limited thermal reaction is carried out in a vacuum, sorbed gases and Langmuir-type monomolecular impurity films are desorbed so as to leave pristine surfaces. Concurrently, soluble complexes of the superconducting oxide particles are formed.

In the demanding world of electrical power devices, very rugged conductors are required. As noted before, the presence of polyvalent metal ions in appropriate complexes can bring about cross-linking of polymeric systems such as I prefer to use. A substantial improvement in the physical characteristics of the system is possible if the cross-linking is of the right type and degree and is reproducible. The cross-linking of my complexes through polyvalent ions offers this opportunity in non-aqueous systems just as I used it earlier in aqueous systems.

The polymerization examples I have given illustrate classic techniques of polymerization. Such basic methods are often modified by the use of various transfer agents, retarders, inhibitors, free-radical initiators, cross-linking agents, etc. so as to secure polymers optimized for various applications. Instead of solution polymerization, emulsion or suspension polymerization can sometimes be advantageously used to make a particular polymer. Further, cross-linking agents such as divinylbenzene are often used in manufacturing proprietary polyacrylic acids. These well known techniques are quite suitable for enhancing basic properties. However, the focus here is on methods of unusual value in producing suitable physical properties.

For compositions of great toughness I have found that it is desirable to still further modify polymeric complexes such as those of the acrylates and MDI which I have described preparing. Earlier I noted that polyfunctional isocyanates such as p-phenylene diisocyanate (PPDI) can be used to cross-link acid alkali metal acrylate copolymers. MDI (diphenylmethane 4,4' diisocyanate or, as it is also designated, methylenediphenyl diisocyanate) can be used as well. The same type of procedure can be used with thallous and similar copolymers.

I have found that there is a kind of equivalent method of cross-linking which can be used to improve the physical characteristics of my reaction products of Polymeric MDI and metal aroylacrylates or their equivalents. In my examples using Polymeric MDI, I have reacted chemical equivalents of my acrylate salt complex and the Polymeric MDI. Thus, I have formed what might be termed "balanced" polymer systems containing neither unreacted acrylate salt nor free NCO groups along the polymeric MDI chains.

Such a polymer no longer has the capacity to react with a variety of "active hydrogen" materials which could readily cross-link with any free NCO groups along the reaction product's chains. It is the equivalent, in terms of reactivity, of the homopolymer metal aroylacrylates I have described earlier which have no free carboxyl groups along their chains to cross-link.

If my reaction products of Polymeric MDI and metal aroylacrylates are prepared with less than an approximately molar equivalent of acrylate salt for each mole of polymeric NCO groups, the resulting polymers then bear free, reactive NCO groups. These are disposed along the chains and are available for cross-linking with a variety of polyfunctional "active hydrogen" materials such as glycols, amines, etc. so as to create a superior polymer. In the same way as with the polymeric acrylates, it is desirable to be able to widely vary the physical properties of the final, cross-linked structures. The use of from 2 to 22% of free isocyanate groups generally gives the desired control. Usually 5 to 10% gives suitable properties.

Though standard active hydrogen materials can be compounded into such free-isocyanate polymeric systems, the cross-linking reaction tends to be so rapid that it poses manufacturing problems. This is especially true if, for example, it is desired to exercise close control over a process such as the printing of circuit boards with a product consisting of a powdered superconducting oxide and a controlled amount of a superconducting organic reaction product matrix. However, if fine control is not desired, with proper equipment suitable materials can be continuously mixed and formed.

A moisture curing, isocyanate-terminated prepolymer that hardens, that is, cures, at ambient temperature by reaction with ambient moisture in the air can also be used, though it poses problems. Such a prepolymer can be based on my reaction products since the "free-isocyanate" material can be treated as a special type of Polymeric MDI. Such a prepolymer, based on the special Polymeric MDI and a polyfunctional polyether, perhaps coordinated with my metal aroyl salts and having a free NCO content of 3–16%, cures from the ambient humidity.

In most cases, the best system is one based on "blocking" the free isocyanate groups of my special polymeric reaction products. They then are inactive as cross-linkers until they are thermally activated by baking and so volatilizing the blocking agent from the material in which they are present, such as the pastes I have mentioned. Such blocked or "capped" isocyanate products, prepared by mixing blocked isocyanates and polyfunctional polyols, have been been used for many years in wire and coil coatings. A variant is to add one of my acid metal aroylacrylate polymers, instead of a polyol, to the blocked isocyanate reaction reaction product since carboxyl groups also react with isocyanate groups.

My materials are unique because of the nature of the special reaction product with its free, though capped-,isocyanate groups. Further, such reaction products can be further modified before thermal activation by coordinating my metal aroyl salts with the oxygen-bearing, pendant groups disposed along the polymeric chains.

As noted, the blocking agents volatilize to activate the NCO groups and a temperature of 120°–160° C. for 10–30 minutes is a typical processing schedule. Alcohols, lactams, ketoximes, and active methylene compounds have all been used successfully. Ethyl acetoacetate, epsilon-caprolactam, and phenol are suitable capping agents, and the amount added is adjusted empirically.

As explained in my copending application Ser. No. 07/821,084, on solvating a liquid crystal precursor a shift to a liquid crystal phase can occur. It can happen when an appropriate amount of a suitable anhydrous solvent ligand reacts with the precursor salt through controlling the vapor pressure of the ligand over a film of the precursor salt. Or a known weight of the precursor salt can be compounded with an appropriate, empirically established, weight of ligand.

On reacting the liquid crystal phase with more anhydrous ligand (by applying the ligand at a higher vapor pressure or by compounding a known weight of liquid crystal complex with additional ligand) the liquid crystal phase dissolves though molecular orientation tends to persist.

These phase shifts are reversible, of course. In the case of nonaqueous ligands, the system's temperature must be adjusted to bring the vapor pressure of the excess ligand to an appropriate level to establish the desired liquid crystal phase. The controlled heating of a paste composition laid down in a thin layer and containing "excess" ligand can readily remove ligand in the proper amount to create oriented liquid crystals in the maximum concentration possible.

Steric factors operate in aligning the molecules into a liquid crystal phase, of course. Thus, adequate time must be allowed for maximum orientation. Electrical and/or magnetic fields can also be used to accelerate and maximize preferred , optimum orientations. If a blocked isocyanate is being used, it is important that liquid crystal orientation be maximized before the isocyanate group is activated by vaporization of the blocking agent with the accompanying cross-linking.

In Example 4 of my copending application Ser. No. 07/642,009, I describe the preparation of a superbly oriented, liquid crystal salt complex system by coordinating my salt complexes with the oxygen groups of a polyetherurethane, isocyanate-terminated prepolymer. A prepolymer of this general type also can be prepared (for further coordination reactions) by first covalently reacting a portion of the isocyanate groups available in Polymeric MDI with my metal aroylacrylate salt complexes as I have described earlier to form a reaction product. Long chain, aliphatic polyethers are then reacted with the remaining free isocyanate groups of the Polymeric MDI. Finally, 5-30% excess MDI is added. As in Example 4, my metal salt complexes can then be added to coordinate with oxygen groups along the polymer chain. If moisture curing is not desired, a blocking agent and a polyol cross-linking agent can be added.

My acid metal aroylacrylate copolymers, with their free carboxyl groups, are able to react with any free isocyanate groups of my reaction products of Polymeric MDI and my metal aroyl acrylate salts, as I have described before. Thus, my copolymers also can be used in the compounding of prepolymers, either in place of or supplementing long chain, aliphatic polyethers.

In another embodiment of my invention I have addressed a problem met in the industrial use of my salt complexes. The problem of laying down useful coatings containing my salts, such as I have just described, is very different from that of efficiently and homogeneously incorporating them into "carrier" plastics. The latter materials can be in the form of fibers, pellets, films, foams, etc. These carrier plastics are often to be used as static dissipative polymers, EMI-control plastics for business machine housings, etc. The concentration of my salt complexes in the final plastic can be as low as 0.1 to 2.0%, depending on the plastic used and the electrical conductivity required. Even if a plastic concentrate is prepared, to be "alloyed" later by compounding with other plastics, the concentration of the salt complex in the concentrate seldom exceeds 20%. In such cases it is very desirable that the dissolving of the carrier plastic be avoided because of the difficulty of stripping ordinary organic solvents from the polymers.

For such applications the use of supercritical fluids to dissolve my metal salt complexes, including the isocyanate reaction products, and to distribute them evenly throughout polymeric systems generally, is of great value. Though I wish to include both the supercritial fluid process and the resulting products with respect to my metal complexes, the use of supercritical carbon dioxide is of special importance. This is because of its low cost, lack of toxicity, and low retention in the plastic. Further, because of its wide use in supercritical extraction processes in the chemical industry, its phase diagram is well known and understood and large scale equipment is readily available for its application.

Supercritical carbon dioxide generally has a low degree of solvency toward plastics, even the ones where it is most active such as atactic hydrocarbon polymers and polymethacrylates with large hydrocarbon branches. However, most plastics are microporous and high pressure carbon dioxide is strongly absorbed by polymers. This typically causes substantial swelling, plasticizing and opening of the system generally. Further, there are myriad voids and micro-cracks in most plastics to begin with.

The diffusibility of carbon dioxide increases greatly as the carbon dioxide sorbs into the polymer. This diffusibility, combined with low viscosity and accompanying swelling, allows material to be infused into the polymer by contacting the polymer with the substance in the presence of the supercritical carbon dioxide under supercritical conditions. The ultimate amount of solute deposited into the polymer depends on the partitioning of the substance between the supercritical fluid-rich phase and the polymer-rich phase. When the pressure is reduced the solute is trapped in the polymer matrix.

My salt complexes can be dissolved first using my triad method when high concentrations of salt complexes need to be introduced into plastics. It is also possible to use finely divided, solid salt complexes directly because the carbon dioxide has the ability to solvate polar materials. Before treatment the powdered complexes must be well distributed throughout the pellets or particles into which most plastics are formed for commercial use. The choice of the form of the material to be dispersed is made empirically, depending on such factors as the type and concentration of salt complex desired in the system, the size of the plastic pellets, and the type of plastic being processed. ABS, polystyrene, polyethylene, polypropylene, polyvinyl chloride, and polycarbonate can be treated. The phase diagram for carbon dioxide is well known, of course, as are the physical properties of the system at various temperatures and pressures.

In another embodiment of my invention I have taken advantage of the special properties of sUpercritical fluids in improving inorganic superconductors. Superconducting oxides are microporous as plastics are, though the microporosity of the crystalline inorganic oxides is quite a different type from that of the organic polymers. In my copending application Ser. No. 07/821,084, I describe how my metal salt complexes can react with metal oxides such as those of inorganic superconductors. In the present application I describe how the aroyl acids of my U.S. Pat. No. 5,082,588 can react with such oxides. Thus, in each case there is a strong driving force to move such materials into the interior of microporous inorganic materials through the displacement of equilibrium through chemical and physical processes. Once inside the microporous particles, my complexes and/or acids can react, fill voids, and bridge gaps between crystals which are only a few molecules wide.

The very low viscosities of supercritical fluids are an important factor in this application, as are the high diffusibility and the zero gas-liquid surface tension because there is no gas-liquid interface. Another factor is the greatly increased solvent power of the fluids as pressure rises, as a result of increased dispersion forces operating in these systems. As with plastics, the rate of pressure reduction after supercritical treatment should be empirically adjusted to maximize the amount and nature of the deposited complexes.

If the superconducting metal oxides are treated with supercritical fluids containing metal complexes immediately after the oxides are manufactured Langmuir-type monomolecular films have not had an opportunity to deposit. Thus, the materials immediately after heat treating are in an ideal form for vacuum/pressure consolidation into various shapes and forms. With an appropriate amount of my blocked isocyanate/metal complex/polyol present in the superconducting oxide/complex mix, the material can be concurrently extruded and heated so as to create sturdy, flexible wires and cables.

I have discovered, as a variant on the in situ procedure described above, that superior products for the manufacture of lithium/sodium polymer electrolyte batteries can be prepared. I have found that the acids of my U.S. Pat. No. 5,082,588 react with alkali metals and especially with their metal foils to create "passivated" surfaces. This is of great value since in the manufacture of alkali metal batteries the reactivity of the high surface area metal foils toward the ambient moisture and carbon dioxide in the manufacturing area has created costly problems.

Further, workers cannot easily work at very low humidities. When they do they generate moisture, carbon dioxide, and myriad active, volatile chemicals which anchor on alkali metal foils and sheets to form Langmuir-type monomolecular films through which ions cannot readily flow. If a metal film, preferably fresh from extrusion, is passed directly into a non-aqueous reaction bath of an appropriate solvent containing the desired aroyl acid(s), a film of the alkali metal salt complex forms and seals the active metal surfaces.

Since the alkylated salt complexes of this application have no response to the humidity levels found in ordinary manufacturing processes, the coated metals are of exceptional inertness. At the same time, the salt complexes form a perfect base on which to deposit cast or extruded polymer electrolytes compounded from my various complexes.

It is important, of course, that the fluid velocity across the metal foil be sufficient to keep the foil clear of bubbles. The bath temperature offers a convenient mode of adjusting the reaction rate for the formation of a homogeneous film deposit. The solvent is readily removed through evaporation.

I claim:

1. A polymeric chemical complex that is the covalent reaction product of the polymerization of
   (a) a lyotropic liquid crystal precursor salt complex that is one or more metal salts of acids having an organic ring structure portion that is hydrophobic and an unsaturated ionic polar head ring complex phase portion that is hydrophilic, the acid having an unsaturated main chain of carbon atoms or carbon atoms and a nitrogen atom, the polar ring complex phase having a ring formed from the keto group of the acid portion, intervening ring members, and a metal ion, the complex having the general structure:

| HYDROPHOBIC ORGANIC RING | HYDROPHILIC, UNSATURATED POLAR RING EQUIVALENT 5 TO 13 MEMBERS |
|---|---| in which the 5 to 13 member ring is formed from the metal (Me) ring member that bonds to the keto group according to the following structure:

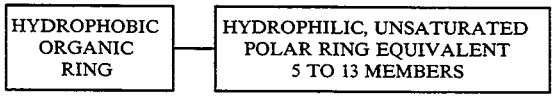

where $R_M$ is one or more ring members when the ring is a 6 to 13 ring member; and the following structure represents the 5 member ring:

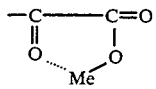

, and
   (b) one or more unsaturated acids as defined in (a).

2. A polymeric chemical complex that is the covalent reaction product of the polymerization of
   (a) a lyotropic liquid crystal precursor salt complex that is one or more metal salts of an acid having an organic ring structure portion that is hydrophobic and a ionic polar head ring complex phase portion that is hydrophilic, the acid having a main chain of carbon atoms or carbon atoms and a nitrogen atom, the polar ring complex phase having a ring formed from the keto group of the acid portion, intervening ring members, and a metal ion, the complex having the general structure:

| HYDROPHOBIC ORGANIC RING | HYDROPHILIC POLAR RING EQUIVALENT 5 TO 13 MEMBERS |
|---|---| in which the 5 to 13 member ring is formed from the metal (Me) ring member that bonds to the keto group according to the following structure:

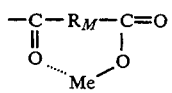

where $R_M$ is one or more ring members when the ring is a 6 to 13 ring member; and the following structure represents the 5 member ring:

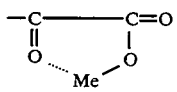

and
   (b) an acid as defined in (a), in which (a) is one or more metal salts of an aroylacrylic acid and (b) is an aroylacrylic acid, there being
   (A) a lattice modifier which comprises one or more of the alkali metal salts of an acid of the general formula R—CZ—(CH$_2$)$_y$—CO$_2$H, where R is amino, hydroxyl, carboxyl or methyl, where Z is hydrogen, hydroxyl, or a keto, and where y is 0 to 4; or
   (B) a lattice stabilizer which comprises a low vapor pressure aryl hydrocarbon from the group consisting of: hydrogenated terphenyl, terphenyl, 1,1-di(ortho-xylyl) ethane, 1,2,3,4 tetramethyl benzene, 1,2,3,5 tetramethyl benzene, 1,2,4,5 tetramethyl benzene, 1,2,3,4,5 pentamethyl-benzene, and cyclohexylbenzene; or
   (C) a lattice stabilizer from the group consisting of alkali metal perfluoroalkyl sulfonates, carboxylates, and acid phosphates, whose fluorocarbon chains contain 3 to 5 carbons.

3. A lyotropic liquid crystal salt complex comprising:
   (a) a polymeric ligand that is a copolymer containing repetitive oxygen-bearing groups along a substantially linear chain, the polymeric chemical complex being the covalent reaction product of the copolymerization of one or more monomeric metal salt complexes of the unsaturated acids of the general formula R—Aryl—CO—X—(CH$_2$)$_y$—CO$_2$H, where R is hydrogen, halogen, alkyl, alkoxy, or nitro, where Aryl is phenyl, biphenyl, naphthalene, acenaphthene, fluorene, anthracene, or pyrene, where X is nitrogen, or a single carbon attached to the adjacent methylene carbon atom with a single bond, and where y is 0 to 7 with the priviso when y is 0, X is —C=C—, the complex having the general structure:

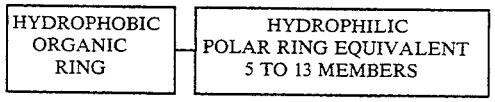

in which the 5 to 13 member rang is formed from the metal (Me) ring member that bonds the keto group according to the following structure:

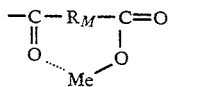

where R$_M$ is one or more ring members when the complex is a 6 to 13 member ring; and the following structure represents the 5 member ring:

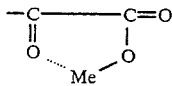

with one or more of the unsaturated acids of (a); and
(b) a non-aqueous, non-polymeric ligand solvent that is an electron donor that forms a coordinate bond by donating electrons to an acceptor metal ion of the polymeric metal salt complex of (a), there being
(A) a lattice modifier which comprises one or more of the alkali metal salts of an acid of the general formula R—CZ—(CH$_2$)$_y$—CO$_2$H, where R is amino, hydroxyl, carboxyl or methyl, where Z is hydrogen, hydroxyl, or a keto, and where y is 0 to 4; or
(B) a lattice stabilizer which comprises a low vapor pressure aryl hydrocarbon from the group consisting of: hydrogenated terphenyl, terphenyl, 1,1-di(ortho-xylyl) ethane, 1,2,3,4 tetramethyl benzene, 1,2,3,5 tetramethyl benzene, 1,2,4,5 tetramethyl benzene, 1,2,3,4,5 pentamethyl-benzene, and cyclohexylbenzene; or
(C) a lattice stabilizer from the group consisting of alkali metal perfluoroalkyl sulfonates, carboxylates, and acid phosphates, whose fluorocarbon chains contain 3 to 5 carbons.

4. A chemical complex comprising:
(a) a lyotropic liquid crystal salt complex that is a metal salt of an acid having an organic ring structure portion that is hydrophobic and an ionic polar head ring complex phase portion that is hydrophilic, the acid having a main chain of carbon atoms or carbon atoms and a nitrogen atom, the polar ring complex phase having a ring formed from the keto group of the acid portion, intervening ring members, and a metal ion, the complex having the general structure:

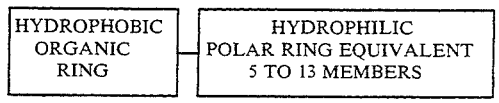

in which the 5 to 13 member ring is formed from the metal (Me) ring member that bonds to the keto group according to the following structure:

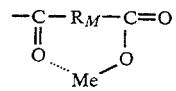

where R$_M$ is one or more ring members when the ring is a 6 to 13 member ring; and the following structure represents the 5 member ring:

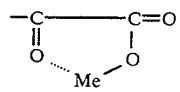

(b) a non-aqueous non-polymeric ligand solvent that forms a coordinate bond as a donor by donating an electron to an acceptor metal of the metal salt complex of (a); and
(c) a polymeric ligand that is a polymer containing repetitive oxygen groups along a substantially linear chain, the polymer being a donor and the salt complex of (a) being an acceptor to form a coordination bond, there being one or more of (A), (B) and (C) as follows
(A) a lattice modifier which comprises one or more of the alkali metal salts of an acid of the general formula R—CZ—(CH$_2$)$_y$—CO$_2$H, where R is amino, hydroxyl, carboxyl or methyl, where Z is hydrogen, hydroxyl, or a keto, and where y is 0 to 4; or
(B) a lattice stabilizer which comprises a low vapor pressure aryl hydrocarbon from the group consisting of: hydrogenated terphenyl, terphenyl, 1,1-di(ortho-xylyl) ethane, 1,2,3,4 tetramethyl benzene, 1,2,3,5 tetramethyl benzene, 1,2,4,5 tetramethyl benzene, 1,2,3,4,5 pentamethyl-benzene, and cyclohexylbenzene; or
(C) a lattice stabilizer from the group consisting of alkali metal perfluoroalkyl sulfonates, carboxylates, and acid phosphates, whose fluorocarbon chains contain 3 to 5 carbons.

5. A lyotrophic liquid crystal complexation product comprising a lyotropic liquid crystal precursor salt complex that is an alkali metal salt of an aryl substituted keto organic acid, the salt having an ionic polar ring complex phase having
(a) an organic aryl ring structure, and
(b) a ring formed from the keto group of the organic acid portion, intervening ring-members, and the alkali metal ion, the ring having at least 5 members in which the alkali metal ion is a ring member that bonds to the keto group to form the ring complex, complexed with 1% to 99% by weight of a finely divided inorganic superconducting oxide compound, the complex having the general structure:

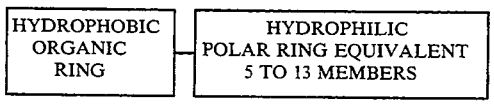

in which the 5 to 13 member ring is formed from the alkali metal (Me) ring member that bonds to the keto group according to the following structure:

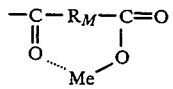

where $R_M$ is one or more ring members when the complex ring is a 6 to 13 member ring; and the following structure represents the 5 member ring:

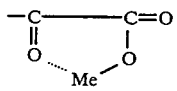

, there being (A) a lattice modifier which comprises one or more of the alkali metal salts of an acid of the general formula $R-CZ-(CH_2)_Y-CO_2H$, where R is amino, hydroxyl, carboxyl or methyl, where Z is hydrogen, hydroxyl, or a keto, and where y is 0 to 4; or (B) a lattice stabilizer which comprises a low vapor pressure aryl hydrocarbon from the group consisting of: hydrogenated terphenyl, terphenyl, 1,1-di(ortho-xylyl) ethane, 1,2,3,4 tetramethyl benzene, 1,2,3,5 tetramethyl benzene, 1,2,4,5 tetramethyl benzene, 1,2,3,4,5 pentamethyl-benzene, and cyclohexylbenzene; or (C) a lattice stabilizer from the group consisting of alkali metal perfluoroalkyl sulfonates, carboxylates, and acid phosphates, whose fluorocarbon chains contain 3 to 5 carbons.

6. A chemical complex comprising (a) one or more alkali metal salts of an acid of the general formula $R-CZ-(CH_2)_Y-CO_2H$, where R is amino, hydroxyl, carboxyl, or methyl, where Z is hydrogen, hydroxyl, or a keto, and where Y is 0 to 4, (b) one or more non-polymeric ligands selected from members of the group comprising the amides, isocyanates, ureas, thioureas, and glycols, and (c) one or more polymeric ligands selected from members of the group of polymers containing repetitive oxygen-bearing groups along a substantially linear chain.

7. A lyotropic liquid crystal salt complex as defined in claim 3 in which A and B are present.

8. A lyotropic liquid crystal salt complex as defined in claim 3 in which A and C are present.

9. A lyotropic liquid crystal salt complex as defined in claim 3 in which A, B and C are present.

10. A lyotropic liquid crystal salt complex as defined in claim 3 in which B and C are present.

* * * * *